(12) United States Patent
Briggs et al.

(10) Patent No.: US 10,368,764 B2
(45) Date of Patent: Aug. 6, 2019

(54) SYSTEM AND METHOD TO SELECT SIGNAL SEGMENTS FOR ANALYSIS OF A BIOLOGICAL RHYTHM DISORDER

(71) Applicant: Topera, Inc., Menlo Park, CA (US)

(72) Inventors: Carey Robert Briggs, La Jolla, CA (US); Ruchir Sehra, Scottsdale, AZ (US)

(73) Assignee: Topera, Inc., Santa Clara, CA (US)

( * ) Notice: Subject to any disclaimer, the term of this patent is extended or adjusted under 35 U.S.C. 154(b) by 677 days.

(21) Appl. No.: 14/483,914

(22) Filed: Sep. 11, 2014

(65) Prior Publication Data

US 2015/0073721 A1 Mar. 12, 2015

Related U.S. Application Data

(60) Provisional application No. 61/877,093, filed on Sep. 12, 2013.

(51) Int. Cl.
*A61B 5/04* (2006.01)
*A61B 5/00* (2006.01)
(Continued)

(52) U.S. Cl.
CPC ........ *A61B 5/04012* (2013.01); *A61B 5/0452* (2013.01); *A61B 5/0464* (2013.01);
(Continued)

(58) Field of Classification Search
CPC ... A61B 5/04012; A61B 5/042; A61B 5/0464; A61B 5/6858; A61B 5/72; A61B 5/7246; A61B 5/0452
(Continued)

(56) References Cited

U.S. PATENT DOCUMENTS 5,109,862 A    5/1992  Kelen et al.
5,217,021 A    6/1993  Steinhaus et al.
(Continued)

FOREIGN PATENT DOCUMENTS

JP    2007-531542 A    11/2007
JP    2008-515486 A     5/2008

OTHER PUBLICATIONS

International Search Report issued in PCT/US2014/055419 dated Feb. 24, 2015.

*Primary Examiner* — Christopher Koharski
*Assistant Examiner* — Pamela M. Bays
(74) *Attorney, Agent, or Firm* — Hoffmann & Baron, LLP

(57) ABSTRACT

A system and method to select segments of cardiac signals. Each of a plurality of segments in a first signal is correlated at a plurality of offsets to determine a highest correlation coefficient for each of the plurality of segments in the first signal. Each of a plurality of segments in a second signal is correlated at the plurality of offsets to determine a highest correlation coefficient for each of the plurality of segments in the second signal. A plurality of composite correlation coefficients is generated using highest correlation coefficients for segments of the first signal and segments of the second signal. The segments of the first and second signals are approximately contemporaneous. A set of segments including a segment from the first signal and a segment from the second signal is selected. The set is associated with a highest composite correlation coefficient from the plurality of composite correlation coefficients.

28 Claims, 14 Drawing Sheets

(51) Int. Cl.
*A61B 5/0452* (2006.01)
*A61B 5/0464* (2006.01)
*A61B 5/042* (2006.01)

(52) U.S. Cl.
CPC ............ *A61B 5/7246* (2013.01); *A61B 5/042* (2013.01); *A61B 5/0422* (2013.01); *A61B 5/6858* (2013.01); *A61B 5/7264* (2013.01); *A61B 2505/05* (2013.01)

(58) Field of Classification Search
USPC .................................................. 600/508, 509
See application file for complete search history.

(56) References Cited

U.S. PATENT DOCUMENTS

| | | | |
|---|---|---|---|
| 5,954,665 A * | 9/1999 | Ben-Haim | A61B 5/06 600/515 |
| 6,950,696 B2 | 9/2005 | Bjorling et al. | |
| 7,283,865 B2 | 10/2007 | Noren | |
| 7,567,837 B2 | 7/2009 | Weil et al. | |
| 2003/0100923 A1* | 5/2003 | Bjorling | A61N 1/3622 607/9 |
| 2004/0127805 A1 | 7/2004 | Macadam et al. | |
| 2006/0149157 A1* | 7/2006 | Weil | A61B 5/046 600/518 |
| 2007/0010753 A1 | 1/2007 | MacAdam | |
| 2012/0283579 A1* | 11/2012 | Briggs | A61B 5/0422 600/484 |
| 2013/0006131 A1* | 1/2013 | Narayan | A61B 5/042 600/508 |

* cited by examiner $$r = \frac{\sum_{i=1}^{n}[(x(i)-\bar{x})*(y(i)-\bar{y})]}{\sqrt{\sum_{i=1}^{n}(x(i)-\bar{x})^2}\sqrt{\sum_{i=1}^{n}(y(i)-\bar{y})^2}}$$

FIG. 9

| Segment | Signal 1 | Signal 2 | Signal 3 | Sum | Mean | SMR |
|---|---|---|---|---|---|---|
| 2-4 msec | $r = 0.73$ | $r = 0.81$ | $r = 0.43$ | 1.97 | 0.66 | 0.65 |
| 3-5 msec | $r = 0.76$ | $r = 0.62$ | $r = 0.47$ | 1.85 | 0.62 | 0.61 |
| 4-6 msec | $r = 0.73$ | $r = 0.54$ | $r = 0.39$ | 1.66 | 0.55 | 0.54 |

FIG. 10

$$\text{SMR} = \left[\sum_{i=1}^{n}\sqrt{x_i}/n\right]^2$$

FIG. 11

SYSTEM AND METHOD TO SELECT SIGNAL SEGMENTS FOR ANALYSIS OF A BIOLOGICAL RHYTHM DISORDER

CROSS REFERENCE TO RELATED APPLICATION

This application claims priority to U.S. Provisional Patent Application No. 61/877,093 filed on Sep. 12, 2013, which is incorporated herein by reference in its entirety.

BACKGROUND

Field

The present application relates generally to biological rhythm disorders. More specifically, the present application is directed to a system and method to select signal segments for analysis of a biological rhythm disorder (e.g., heart rhythm disorder).

Brief Discussion of Related Art

Biological rhythm disorders, such as heart (cardiac) rhythm disorders, are common and represent significant causes of morbidity and death throughout the world. Malfunction of the electrical system in the heart represents a proximate cause of the heart rhythm disorders. Heart rhythm disorders exist in many forms, of which the most complex and difficult to treat are atrial fibrillation (AF), ventricular tachycardia (VT) and ventricular fibrillation (VF). Other rhythm disorders are more simple to treat, but may also be clinically significant including atrial tachycardia (AT), supraventricular tachycardia (SVT), atrial flutter (AFL), supraventricular ectopic complexes/beats (SVE) and premature ventricular complexes/beats (PVC).

Previously, treatment of heart rhythm disorders—particularly complex rhythm disorders of AF, VF and polymorphic VT—has been difficult because the location in the heart that harbors the source of the heart rhythm disorder could not be identified. There have been various theories of how complex rhythm disorders function and clinical applications for treating these complex rhythm disorders. However, none of the applications proved fruitful in the treatment of complex rhythm disorders.

Recently, there has been a breakthrough discovery that for the first time identified sources associated with complex heart rhythm disorders. This technological breakthrough successfully analyzed and reconstructed cardiac activation information (activation onset times) in signals obtained from electrodes of catheters introduced into the patient's heart to identify rotational activation patterns (rotational sources such as rotors), as well as focal sources, which cause and sustain a large percentage of the heart rhythm disorders worldwide. Treatment of the heart rhythm disorders can thus be targeted to the rotational and/or focal sources in the patient's heart to eliminate the heart rhythm disorders. Such treatment can be successfully delivered by ablation, for example.

As aforementioned, cardiac signals are generally obtained (e.g. sensed, acquired, or recorded) from electrodes of catheters introduced into the patient's heart. Many sources of noise are often embedded or superimposed in the signals when the signals are obtained from the patient. These sources can include electrical activity from another part of the patient's heart, other anatomic structures of the patient, motion artifacts from movement of the electrodes and/or movement of the patient (e.g., breathing), mechanical crosstalk resulting from electrodes contacting each other, saturation of electronic amplifiers, radio frequency (RF) energy from external systems, as well as other sources of noise. In addition, the electrodes can have various levels of contact (or non-contact) with the patient's heart that can reduce the amplitude of the signals and, in the worst cases, can even result in the absence of electrical activity in the signals.

Reconstruction of the cardiac activation information (activation onset times) requires analyses of the signals that can be computationally-intensive as well as time-intensive. It may not be advantageous due to these or other computational constraints to analyze the entirety of the signals. Moreover, certain portions of these signals—in some cases, extensive portions—can be affected by noise. In such circumstances, it is may be advantageous to avoid portions the signals where analysis is complex and limited by noise superimposed in the signals.

Analysis of the entirety of these signals can affect negatively the time and accuracy in identifying a source of a heart rhythm disorder, as well as the accuracy in targeting of the source of the heart rhythm disorder for treatment and elimination.

Accordingly, it is desirable to identify portions of these signals (e.g., signal segments) that include periodic cardiac information with the reduced amount of noise for further analysis, which can improve the time and accuracy in identifying the source of a heart rhythm disorder, as well as the time and accuracy in the targeting of the source of the heart rhythm disorder for treatment and elimination.

SUMMARY

The present application is applicable to the selection of a set of signal segments from a plurality of signals obtained from a patient that include minimum noise and stable, well-defined biological activity for detection and treatment of a cause or source of a rhythm disorder in the patient. The signal segment selection is applicable various rhythm disorders, including heart rhythm disorders, as well as other biological rhythm disorders, such as neurological seizures, esophageal spasms, bladder instability, irritable bowel syndrome, and other biological disorders for which signal segments can be selected from a plurality of signals to permit determination, diagnosis, and/or treatment of the cause or source of the disorders. It is particularly useful, however, in complex rhythm disorders which result in complex activation patterns, and especially useful in complex rhythm disorders of the heart, to improve detection of the cause(s) or source(s) of the disorders such that they can be treated with expediency.

Complex heart rhythm disorders typically result in activation patterns that are extremely difficult to decipher and the ability to determine accurate activation information of heartbeats in complex disorders has previously not been possible. Among the advantages of the present application is the ability to select signal segments from a plurality of signals that have minimum noise and stable, well-defined biological activity such that a determination of the cause and/or source of the rhythm disorder can be determined and treated more quickly and with greater precision. Another advantage is that the application provides a system and method which can be carried out rapidly while a sensing device—such as a catheter having sensors thereon—is used in or near the patient and can be followed by signal segment selection, determination of the source of the rhythm disorder based on the selected signal segments and treatment of the cardiac tissue to ameliorate the rhythm disorder and, in many cases, cure the disorder.

In accordance with an embodiment or aspect, a method of selecting signal segments of multiple cardiac signals is disclosed.

A signal segment in at least one first cardiac signal is correlated to the signal segment itself as shifted by a plurality of time offsets to determine a highest correlation coefficient associated with periodicity of the signal segment in the at least one first cardiac signal.

A signal segment in at least one second cardiac signal is correlated to the signal segment itself as shifted by the plurality of time offsets to determine a highest correlation coefficient associated with periodicity of the signal segment in the at least one second cardiac signal.

The correlating is repeated for additional signal segments in the at least one first cardiac signal and additional signal segments in the at least one second cardiac signal to determine a highest correlation coefficient associated with periodicity of each of the additional signal segments.

A plurality of composite correlation coefficients is generated using highest correlation coefficients for the signal segments of the at least one first cardiac signal and the signal segments of the at least one second cardiac signal. Each of the plurality of composite correlation coefficients is associated with signal segments of the at least one first cardiac signal that are approximately contemporaneous with signal segments of the at least one second cardiac signal.

A set of signal segments including at least one signal segment from the at least one first cardiac signal and at least one signal segment from the at least one second cardiac signal is selected. The set of signal segments is associated with a highest composite correlation coefficient from the plurality of composite correlation coefficients.

In accordance with the method, the set of signal segments can also be processed to determine a source of a rhythm disorder.

In accordance with another embodiment or aspect, a system to select signal segments of cardiac signals is disclosed. The system includes a processing device and a memory. The memory device stores instructions that, when executed by the processing device, cause the processing device to perform the following operations.

A signal segment in at least one first cardiac signal is correlated to the signal segment itself as shifted by a plurality of time offsets to determine a highest correlation coefficient associated with periodicity of the signal segment in the at least one first cardiac signal.

A signal segment in at least one second cardiac signal is correlated to the signal segment itself as shifted by the plurality of time offsets to determine a highest correlation coefficient associated with periodicity of the signal segment in the at least one second cardiac signal.

The correlating is repeated for additional signal segments in the at least one first cardiac signal and additional signal segments in the at least one second cardiac signal to determine a highest correlation coefficient associated with periodicity of each of the additional signal segments.

A plurality of composite correlation coefficients is generated using highest correlation coefficients for the signal segments of the at least one first cardiac signal and the signal segments of the at least one second cardiac signal. Each of the plurality of composite correlation coefficients is associated with signal segments of the least one first cardiac signal that are approximately contemporaneous with signal segments of the at least one second cardiac signal.

A set of signal segments including at least one signal segment from the at least one first cardiac signal and at least one signal segment from the at least one second cardiac signal is selected. The set of signal segments is associated with a highest composite correlation coefficient from the plurality of composite correlation coefficients.

The operations can also include processing the set of signal segments to determine a source of a cardiac rhythm disorder.

These and other purposes, goals and advantages of the present application will become apparent from the following detailed description read in connection with the accompanying drawings.

BRIEF DESCRIPTION OF THE DRAWINGS

Some embodiments or aspects are illustrated by way of example and not limitation in the figures of the accompanying drawings in which:

FIG. 9 illustrates an example correlation calculation for a given time offset, such as 100 msec;

FIG. 10 illustrates an example table that summarizes highest correlation coefficients (r) for the signal segments in each of the signals in FIG. 2;

FIG. 11 illustrates an example calculation for the square-mean-root of the highest correlation coefficients (r);

DETAILED DESCRIPTION

A system and method to select signal segments for analysis of a biological rhythm disorder (e.g., heart rhythm disorder) are disclosed herein. In the following description, for the purposes of explanation, numerous specific details are set forth in order to provide a thorough understanding of example embodiments or aspects. It will be evident, however, to one skilled in the art, that an example embodiment may be practiced without all of the disclosed specific details.

Figure 1:
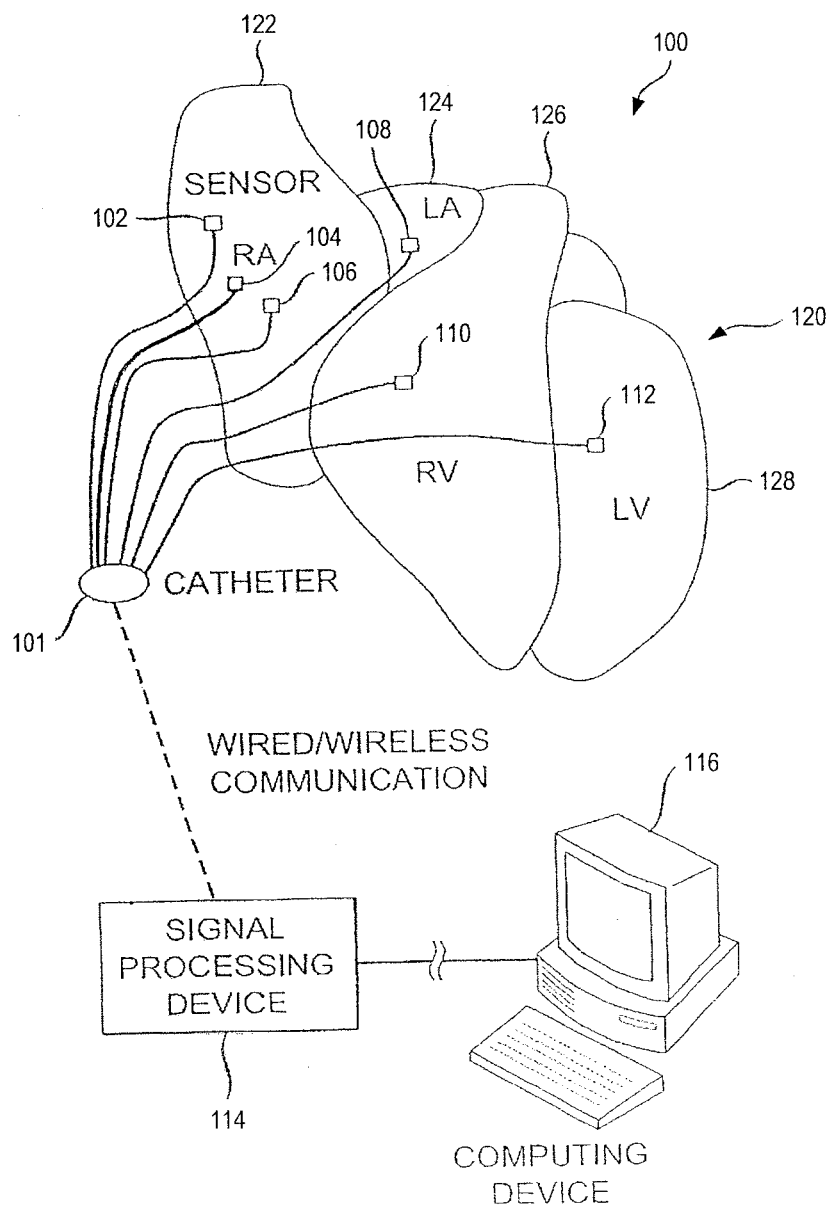
FIG. 1 illustrates an example signal processing system.

FIG. 1 illustrates an example signal processing system 100. The example system 100 is configured to detect signals from a patient's heart in connection with a heart rhythm disorder, and to select signal segments from these signals that include periodic cardiac activation information with the reduced amount of noise for further analysis, which can improve the time and accuracy in identifying the source of a heart rhythm disorder, as well as the time and accuracy in the targeting of the source of the heart rhythm disorder for treatment and elimination. The heart includes a right atrium 122, left atrium 124, right ventricle 126 and left ventricle 128. The example system 100 includes a catheter 101, signal processing device 114 and a computing device 116.

The catheter 101 is configured to detect cardiac activation information in the heart and to transmit the detected cardiac activation information to the signal processing device 114, either via a wireless or wired connection. The catheter includes a plurality of electrodes or sensors 102-112, which can be inserted into the heart through the patient's blood vessels.

In some embodiments or aspects, one or more of the sensors 102-112 are not inserted into the patient's heart. For example, some sensors may detect cardiac activation via the patient's surface (e.g., electrocardiogram, body surface mapping) or remotely without contact with the patient (e.g., magnetocardiogram). As another example, some sensors may also derive cardiac activation information from cardiac motion of a non-electrical sensing device (e.g., echocardiogram). In various embodiments or aspects, these sensors can be used separately or in different combinations, and further these separate or different combinations can also be used in combination with sensors inserted into the patient's heart.

The sensors 102-112, which are positioned at certain locations (sensor locations) in the heart under consideration, can detect cardiac activation information at sensed locations and can further deliver energy to ablate the heart at these sensed locations. A sensed location is an area located proximately to and including a sensor location from which a sensor detects cardiac activation information. It is noted that the sensors 102-112 can also detect cardiac activation information from overlapping regions of the heart (e.g., right atrium 122 and left atrium 124).

The signal processing device 114 is configured to process (e.g., clarify and amplify) the cardiac activation information detected by the sensors 102-112 at the sensed locations into electrogram signals (hereinafter "signals") and to provide the processed signals to the computing device 116 for segment selection and further analysis as disclosed herein. In processing the cardiac activation information from the sensors 102-112, the signal processing device 114 can subtract cardiac activation information from overlapping regions of the heart 120 to provide the processed signals to the computing device 116 for analysis. While in some embodiments or aspects, the signal processing device 114 is configured to provide unipolar signals, in other embodiments or aspects, the signal processing device 114 can provide bipolar signals.

As aforementioned, the activation information detected by the sensors 102-112 can include embedded or superimposed noise. The computing device 116 is configured to receive or access the signals from the signal processing device 114, and in some embodiments, the computing device 116 is configured to select epochs (windows) of certain length from the received or accessed signals, which herein are also considered to be signals. The computing device 116 is further configured to automatically select segments of the signals (hereinafter "signal segments") with reduced amount of noise in accordance with methods, functions or logic disclosed for identifying a source of a heart rhythm disorder. Specifically, the selected signal segments can be used to improve the time and accuracy of identifying a source of a heart rhythm disorder, as well as the time and accuracy in the targeting of the source of the heart rhythm disorder for treatment and elimination. For example, the selected signal segments can be processed as input signals by U.S. Pat. No. 8,165,666 to Briggs, et al., the subject matter of which is incorporated herein by reference in its entirety.

Figure 2:
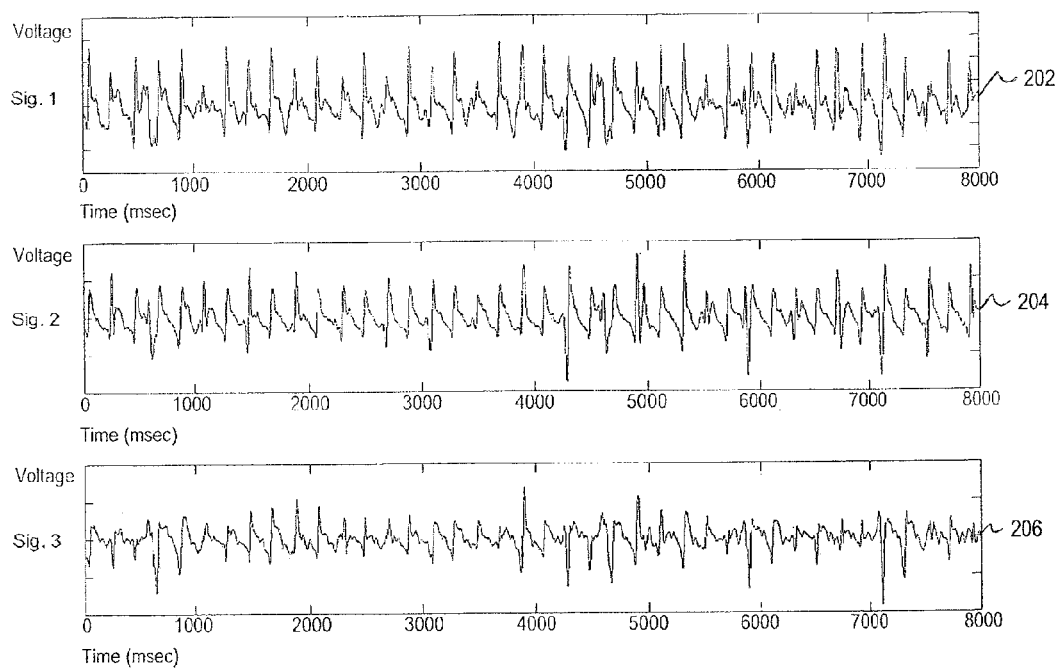
FIG. 2 illustrates example electrogram signals of a complex heart rhythm disorder obtained approximately contemporaneously from the example sensors positioned at sensed locations in a patient's heart of FIG. 1.

FIG. 2 illustrates example signals 202-206 of a complex heart rhythm disorder obtained approximately contemporaneously (e.g., at or about the same time) in connection with the example sensors 102-106 positioned at sensed locations in the heart 120 of FIG. 1, according to a first embodiment. For example, sensors 102-106 of catheter 101 can be positioned at sensed locations in the right atrium 122, as illustrated in FIG. 1. As an example, the heart rhythm disorder can be a complex rhythm disorder AF, VF and polymorphic VT, or another heart rhythm disorder.

The computing device 116 receives, accesses, otherwise selects the example signals 202-206. The example signals 202-206 are illustrated to be eight (8) seconds in length to provide a brief yet clear illustration. However, the signals 202-206 can also be sixty (60) seconds, or another longer or shorter period. It should also be noted, however, that the signals received or accessed by the computing device 116 can be any length, e.g., having a discrete length or being continuous in length. In some embodiments, the signals 202-206 can represent epochs (windows) of a certain length of time selected by the computing device 116 from such received or accessed signals, e.g., the signals 202-206 thus selected can be sixty (60) seconds, or another longer or shorter period. The signals 202-206 are associated with the example sensors 102-106 positioned at the sensed locations in the heart 120 during a complex heart rhythm disorder, as for example illustrated in FIG. 1. It is noted that multiple signals can be provided by the catheter 101, e.g., 64 signals from corresponding sensors of a basket catheter can provide a panoramic view of the right atrium 122 of the heart 120.

Based on example observations in certain heart rhythm disorders (e.g., AF), cycle length of about 100 msec to about 300 msec between activation onsets is typically observed in a signal at a particular sensor (sensed location) during such heart rhythm disorders. Based on example observations in certain other heart rhythm disorder (e.g., AT, AFL), the cycle length is generally higher (e.g., about 300 msec to about 500 msec). In normal sinus rhythms, the cycle length between activation onsets is generally even higher (e.g., about 600 msec to about 1000 msec). In this example embodiment, the signals 202-206 are associated with cycle lengths in a range of 100 msec-350 msec.

Activation onsets in the signal are generally identifiable as having a small degree of change in the signal from baseline superimposed in the signal that is local to the sensed location with few far-field artifacts that could be mistaken as local activity in the signal. Local activity at the sensed location can be characterized in the signal by an activation onset with a sharp inflection point and high slope, followed by a period of gentle, low-deviation slope representing repolarization, typically lasting between about 100 msec and 250 msec in some of the example observations (e.g., atrial fibrillation), and longer in other example observations (e.g., atrial tachycardia).

Multiple deflections of short duration (e.g., shorter than the shortest cycle length of about 100 msec) can make the discernment of local activation onsets at the sensed location as opposed to far-field activations or simply noise prohibitively difficult. For example, in the first 1,000 msec of Sig. 1 (reference 202), eight or so deflections are present and can possibly indicate activation onsets. It should be noted, however, that the heart 120 cannot physiologically activate again after an activation onset (deflection) detected at the sensed location in a cycle length shorter than about 100 msec to about 300 msec because the tissue of the heart 120 local to the sensed location must undergo repolarization. It is noted that the deflection cannot be local to the sensed location when this deflection is also significantly present in signals detected at neighbor sensed locations to this sensed location.

Moreover, processing of the entirety of the signals 202-206 can be very time intensive and computationally intensive, and can further increase the time and limit the ability to identify the source of complex the heart rhythm disorder in the heart 120. It is thus desirable to select corresponding signal segments in the signals 202-206 that include periodic cardiac activation information with the reduced amount of far-field activations and noise for further analysis, which can improve the time and accuracy in identifying the source of a heart rhythm disorder, as well as the time and accuracy in the targeting of the source of the heart rhythm disorder for treatment and elimination.

The system and method described herein automate signal segment selection in the signals 202-206 using a correlation calculation (e.g., autocorrelation) over a selected range of time offsets (e.g., 100 msec-350 msec) to determine programmatically a set of corresponding signal segments in the signals 202-206 that are aggregately most correlated from a plurality of signal segments in these signals 202-206, for further analysis and identification of the source of a heart rhythm disorder.

It is noted that the selected range of time offsets is slightly wider (e.g., 350 msec) than the example cycle length (e.g., 300 msec used for illustration of an associated complex rhythm disorder in this embodiment), which mitigates the possibility of missing correlation close to or about the end of the example cycle length (e.g., 300 msec). Similarly, the selected range of time offsets can be adjusted to be slightly wider at the beginning (e.g., 50 msec) to mitigate the possibility of missing correlation close to or about the beginning of the example cycle length (e.g., 100 msec). In some cases, the range of time offsets selected can equal or approximate the described example cycle length associated with cardiac rhythm disorders of this embodiment (e.g., 100 msec to 300 msec).

Moreover, the range of time offsets can be selectively varied based on one or more particular cardiac rhythms disorder (e.g., AF, VT, VF), as well as one or more other biological rhythm disorders (e.g., neurological seizures, esophageal spasms, bladder instability, irritable bowel syndrome, and other biological disorders).

In this example embodiment, the minimum and maximum time offsets for the correlation calculation have been selected to be 100 msec and 350 msec, respectively. The minimum and maximum offsets approximate the outer cycle lengths of 100 msec and 300 msec described hereinabove for example complex rhythm disorders of this embodiment. As a result, the periodicity of the signal segment contributing to the correlation coefficient (r) will have a cycle length between about 100 msec and about 300 msec.

An example correlation calculation will be described in greater detail herein with reference to FIG. 9. At this point it is sufficient to mention that the correlation calculation correlates (e.g., auto-correlates) each signal segment with itself over the range of the time offsets, e.g., 100 msec-350 msec, to determine a plurality of correlation coefficients (r) at the plurality of offsets in the signal segment. A highest (maximum) correlation coefficient (r) from the plurality of coefficients is recorded for the signal segment. The example range of time offsets and corresponding correlation coefficients (r) of this embodiment will be described in greater detail herein with reference to FIGS. 6 and 7. It is noted that different correlation methods or techniques can be used to correlate (e.g., auto-correlate) each signal segment with itself over the range of the time offsets.

A signal segment with minimal noise and well-defined cardiac activity will have a higher correlation coefficient (r) than a signal segment with a significant amount of noise superimposed over the cardiac activity. Accordingly, selection of corresponding (approximately contemporaneous) signal segments in the signals 202-206 having a highest composite correlation (r) across all signals 202-206 will provide a set of signal segments having best signal quality across all of the signals 202-206 for further analysis that will detect underlying cardiac activation information (activation onset times), which can improve the time and accuracy in identifying the source of a heart rhythm disorder, as well as the time and accuracy in the targeting of the source of the heart rhythm disorder for treatment and elimination.

Figure 3:
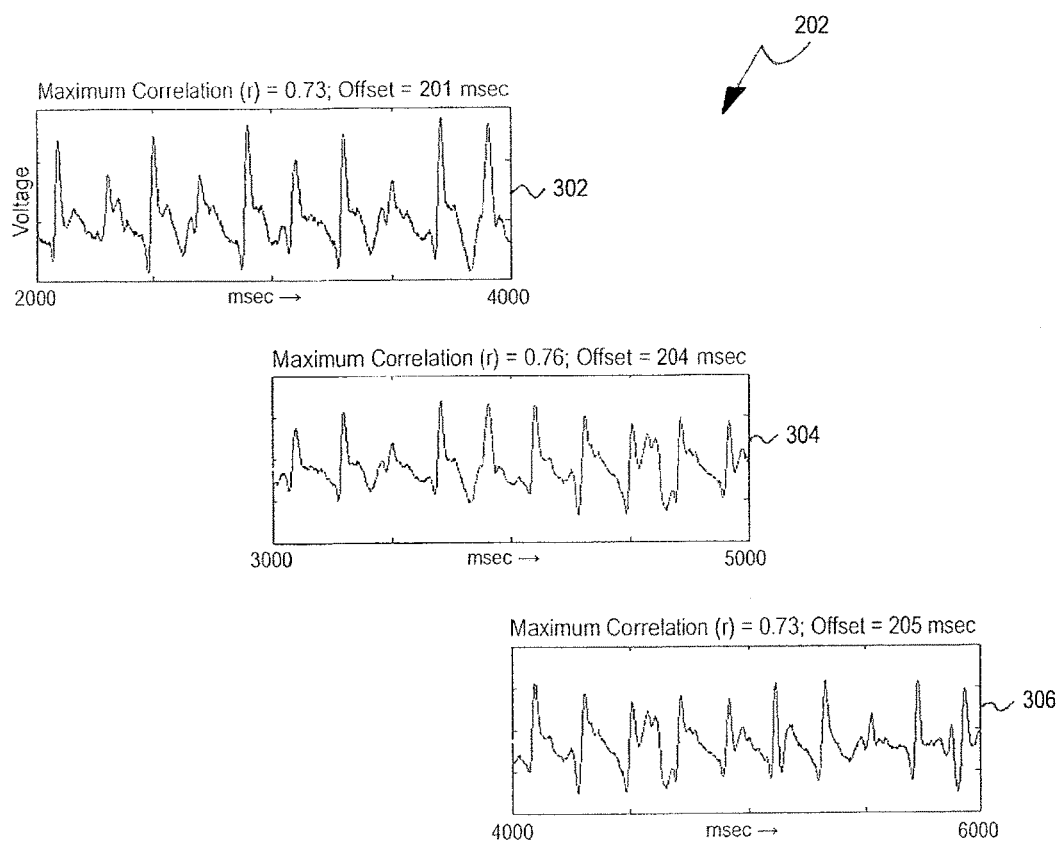
FIG. 3 illustrates an example first signal of FIG. 2 segmented into example three segments.

FIG. 3 illustrates the example first signal 202 of FIG. 2 segmented into example three (3) segments 302-306. Only three segments 302-306 are illustrated for brevity and clarity. As noted in reference to FIG. 2, the first signal 202 is eight (8) seconds in length. A different length is of course possible, e.g., 60 seconds or more.

Each of the example signal segments 302-306 is two (2) seconds in length (hereinafter "segment length"). As illustrated in FIG. 3, the signal segments 302-306 can overlap at least partially. For example, signal segment 302 is 2 msec-4 msec, signal segment 304 is 3 msec-5 msec, and signal segment 306 is 4 msec-6 msec. It is noted that the first signal 202 can be segmented into additional overlapping signal segments of the foregoing segment length, e.g., 0 msec-2 msec, 1 msec-3 msec, 5 msec-7 msec, and 6 msec-8 msec.

It is further noted that a different segment length of the signal segments 302-306 can be selected based on the overall length of the first signal 202, for example. As an example, the first signal 202 can be segmented into signal segments of four (4) seconds in lengths that can also overlap at least partially, e.g., 0 msec-4 msec, 1 msec-5 msec, 2 msec-6 msec, 3 msec-7 msec, 4 msec-8 msec.

Each of the signal segments 302-306 is correlated with itself (e.g., using correlation calculation of FIG. 9) over a selected range of the time offsets to determine a plurality of correlation coefficients (r) at the plurality of offsets in each of the signal segments 302-306. The range of time offsets is associated with a cycle length of a biological rhythm disorder (e.g., heart rhythm disorder). In accordance with this embodiment, the range is selected to be 100 msec-350 msec.

A highest (maximum) correlation coefficient (r) from the plurality of correlation coefficients is recorded for each of the signal segments 302-306. As illustrated in FIG. 3, the maximum correlation coefficient (r=0.73) for the signal segment 302 is obtained at offset 201 msec. For the signal segment 304, the maximum correlation coefficient (r=0.76) is obtained at offset 204 msec. Lastly, for the signal segment 304, the maximum correlation coefficient (r=0.73) is obtained at offset 205 msec.

Figure 4:
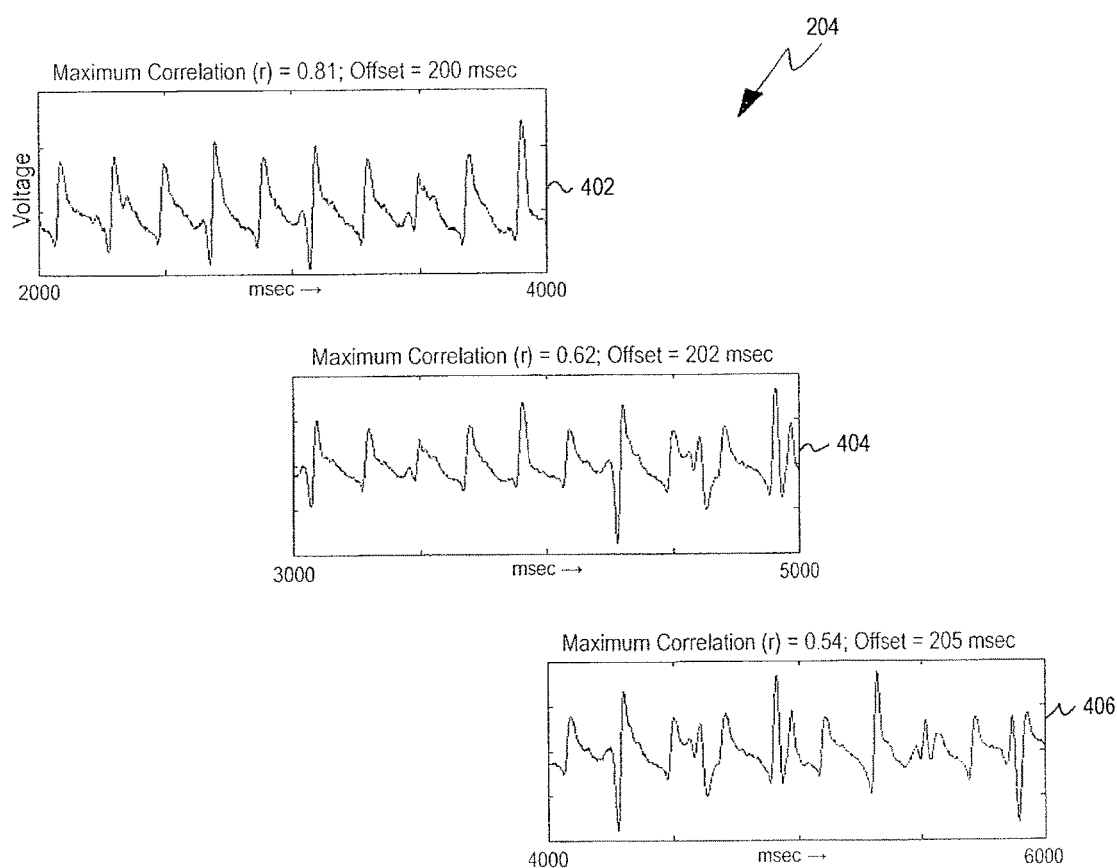
FIG. 4 illustrates an example second signal of FIG. 2 segmented into example three segments.

FIG. 4 illustrates the example second signal 204 of FIG. 2 segmented into example three (3) segments 402-406. Only three segments 402-406 are illustrated for brevity and clarity. Each of the example signal segments 402-406 has a two (2) second segment length.

As illustrated in FIG. 4, the signal segments 402-406 can overlap at least partially. For example, signal segment 402 is 2 msec-4 msec, signal segment 404 is 3 msec-5 msec, and signal segment 406 is 4 msec-6 msec. It is noted that the second signal 204 can be segmented into additional, at least partially overlapping, signal segments of the foregoing segment length, e.g., 0 msec-2 msec, 1 msec-3 msec, 5 msec-7 msec, and 6 msec-8 msec.

A different segment length of the signal segments 402-406 can be selected as described with reference to the first signal 202 in FIG. 3. For example, the second signal 204 can also be segmented into signal segments of four (4) seconds in lengths that can also overlap at least partially, e.g., 0 msec-4 msec, 1 msec-5 msec, 2 msec-6 msec, 3 msec-7 msec, 4 msec-8 msec.

Each of the signal segments 402-406 is correlated with itself (e.g., using correlation calculation of FIG. 9) over the range of the time offsets (e.g., 100 msec-350 msec) to determine a plurality of correlation coefficients (r) at the plurality of offsets in each of the signal segments 402-406. A highest (maximum) correlation coefficient (r) from the plurality of correlation coefficients is recorded for each of the signal segments 402-406. As illustrated in FIG. 4, the maximum correlation coefficient (r=0.81) for the signal segment 402 is obtained at offset 200 msec. For the signal segment 404, the maximum correlation coefficient (r=0.62) is obtained at offset 202 msec. Lastly, for the signal segment 406, the maximum correlation coefficient (r=0.54) is obtained at offset 205 msec.

Figure 5:
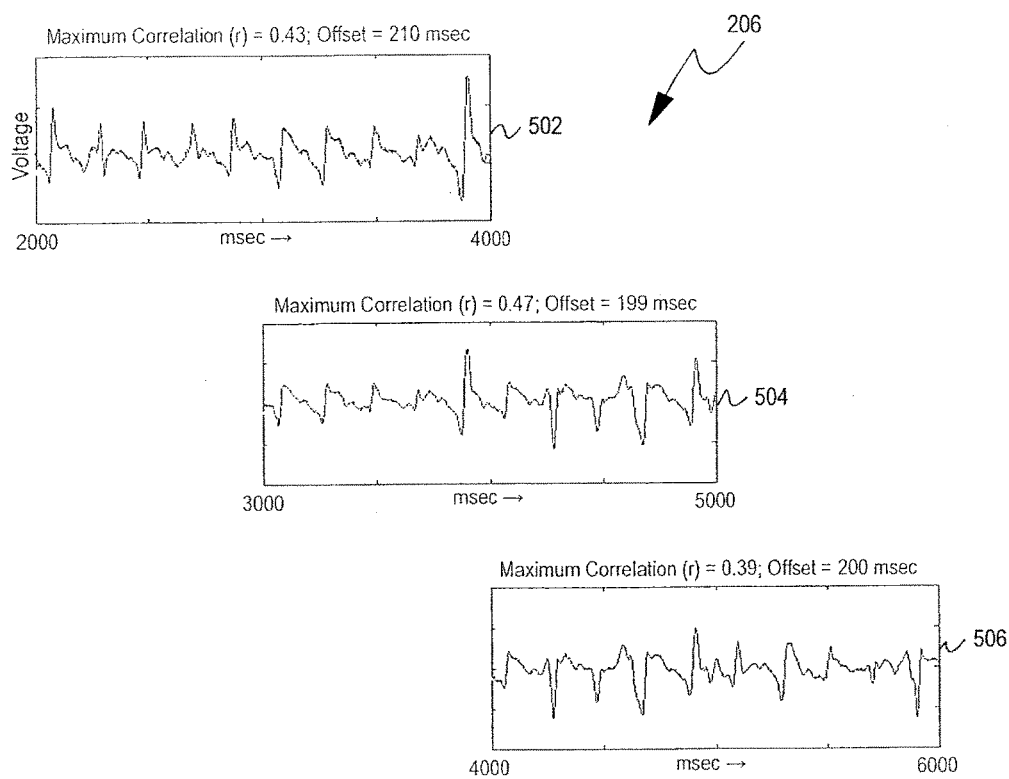
FIG. 5 illustrates an example third signal of FIG. 2 segmented into example three segments.

FIG. 5 illustrates the example third signal 206 of FIG. 2 segmented into example three (3) segments 502-506. Only three segments 502-506 are illustrated for brevity and clarity. Each of the example signal segments 502-506 has a two (2) second segment length.

As illustrated in FIG. 5, the signal segments 502-506 can overlap at least partially. For example, signal segment 502 is 2 msec-4 msec, signal segment 504 is 3 msec-5 msec, and signal segment 506 is 4 msec-6 msec. It is noted that the third signal 206 can be segmented into additional, partially overlapping signal segments of the foregoing segment length, e.g., 0 msec-2 msec, 1 msec-3 msec, 5 msec-7 msec, and 6 msec-8 msec.

A different length of the signal segments 502-506 can be selected as described with reference to the first signal 202 in FIG. 3. For example, the third signal 206 can also be segmented into signal segments of four (4) seconds in lengths that can also overlap at least partially, e.g., 0 msec-4 msec, 1 msec-5 msec, 2 msec-6 msec, 3 msec-7 msec, 4 msec-8 msec.

Each of the signal segments 502-506 is correlated with itself (e.g., using correlation calculation of FIG. 9) over the range of the time offsets (e.g., 100 msec-350 msec) to determine a plurality of correlation coefficients (r) at the plurality of offsets in each of the signal segments 502-506. A highest (maximum) correlation coefficient (r) from the plurality of coefficient coefficients is recorded for each of the signal segments 502-506. As illustrated in FIG. 5, the maximum correlation coefficient (r=0.43) for the signal segment 502 is obtained at offset 210 msec. For the signal segment 504, the maximum correlation coefficient (r=0.47) is obtained at offset 199 msec. Lastly, for the signal segment 506, the maximum correlation coefficient (r=0.39) is obtained at offset 200 msec.

Figure 6:
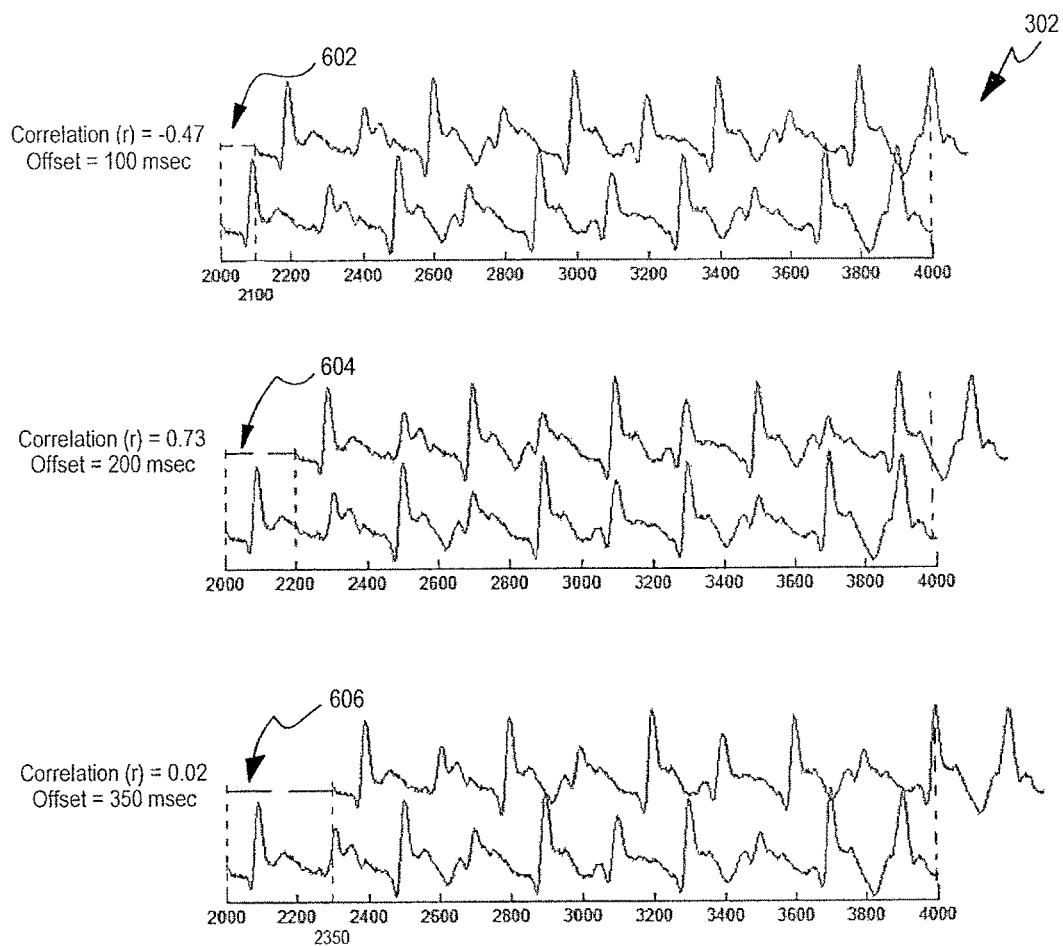
FIG. 6 illustrates three example time shifts (or offsets) in the first example signal segment in FIG. 3 of the first signal in FIG. 2.

FIG. 6 illustrates three (3) example time shifts (or offsets) 602-606 in the first example signal segment 302 in FIG. 3 of the first signal 202 in FIG. 2.

For example, the first time offset 602 is 100 msec, the second time offset 604 is 200 msec, and the third time offset 602 is 350 msec. It is noted that there can be 250 time offsets in the range of 100 msec-350 msec, using an increment of one (1) msec.

A correlation coefficient (r) is calculated for each of the time offsets in the range 100 msec-350 msec using the example correlation calculation of FIG. 9. For example, at the lower time offset of 100 msec, the correlation coefficient (r)=−0.47, and at the upper offset of 350 msec, the correlation coefficient (r)=0.02. The maximum correlation coefficient (r)=0.73 is obtained at the offset of 200 msec, as illustrated in FIG. 6. It is noted that a different correlation method or technique can be used to correlate (auto-correlate) the example signal segment 302 with itself.

As an example, the signal segment is correlated with itself using the example correlation calculation of FIG. 9. Specifically, the correlation can be described as the summation of the product of two discrete data series (representing a voltage element at each msec in the signal segment). Correlation coefficients (e.g., numerical result of the correlation) are normalized to a range −1 to 1.

In one embodiment, for a given a signal segment (e.g., signal segment 302), correlation at a given time offset t (e.g., 100 msec) can be calculated by generating two reference segments from the original signal segment: the first reference segment with t elements (e.g., each element one (1) msec) removed from the beginning of the given signal segment, and the other reference segment with t elements (e.g., each element one (1) msec) removed from the end the given signal segment. The correlation coefficient (r) for the given time offset t is thus determined based on the reference segments, e.g., using the example correlation calculation illustrated in FIG. 9.

In another embodiment, one reference signal segment is generated for a given signal segment (e.g., signal segment 302) at a given time offset t (e.g., 100 msec), which extends from the beginning of the given signal segment to an ending represented by the end of the given signal segment minus the given offset t. The correlation coefficient (r) for the given time offset t is thus determined based on the given signal segment that extends from the time offset to the end of the signal segment and the reference signal segment, e.g., using the example correlation calculation illustrated in FIG. 9.

It should be noted that the signals segments 302-306, 402-406, 502-506 of the respective signals 202, 204, 206 are processed to calculate a correlation coefficient (r) for each of the time offsets in the range 100 msec-350 msec, as described hereinabove with reference to the signal segment 302.

Figure 7:
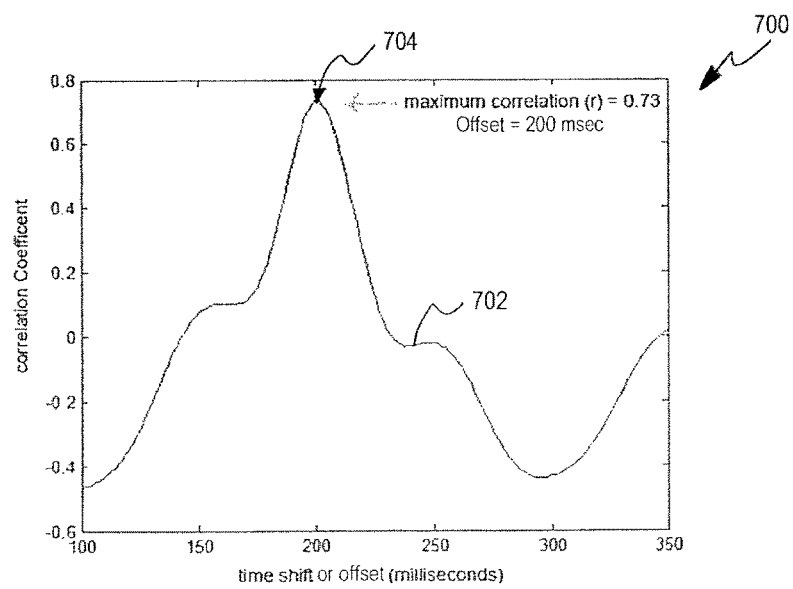
FIG. 7 illustrates an example graph showing a curve of the correlation coefficients (r) determined for the time offsets in the range 100 msec to 350 msec in the first signal segment in FIG. 3 of the first signal in FIG. 2.

FIG. 7 illustrates an example graph 700 showing a curve 702 of the correlation coefficients (r) determined for the time offsets in the range 100 msec to 350 msec in the signal first segment 302 in FIG. 3 of the first signal 202 in FIG. 2.

As illustrated in FIG. 7, correlation coefficients are between −0.47 to 0.02 in the range of time offsets between 100 msec-350 msec, with the maximum correlation coefficient (r)=0.73 occurring at the time offset of 200 msec.

It should be noted that a similar curve can be generated to illustrate correlation coefficients (r) determined for the time offsets in the range 100 msec to 350 msec for other signals segments 304, 306 of signal 202, as well as the signal segments 402-406, 502-506 of the other signals 204, 206. What is important to note is that a maximum correlation coefficient (r) is determined for each signal segment (302-306, 402-406, 502-506) of each of the respective signals (202, 204, 206).

Figure 8:
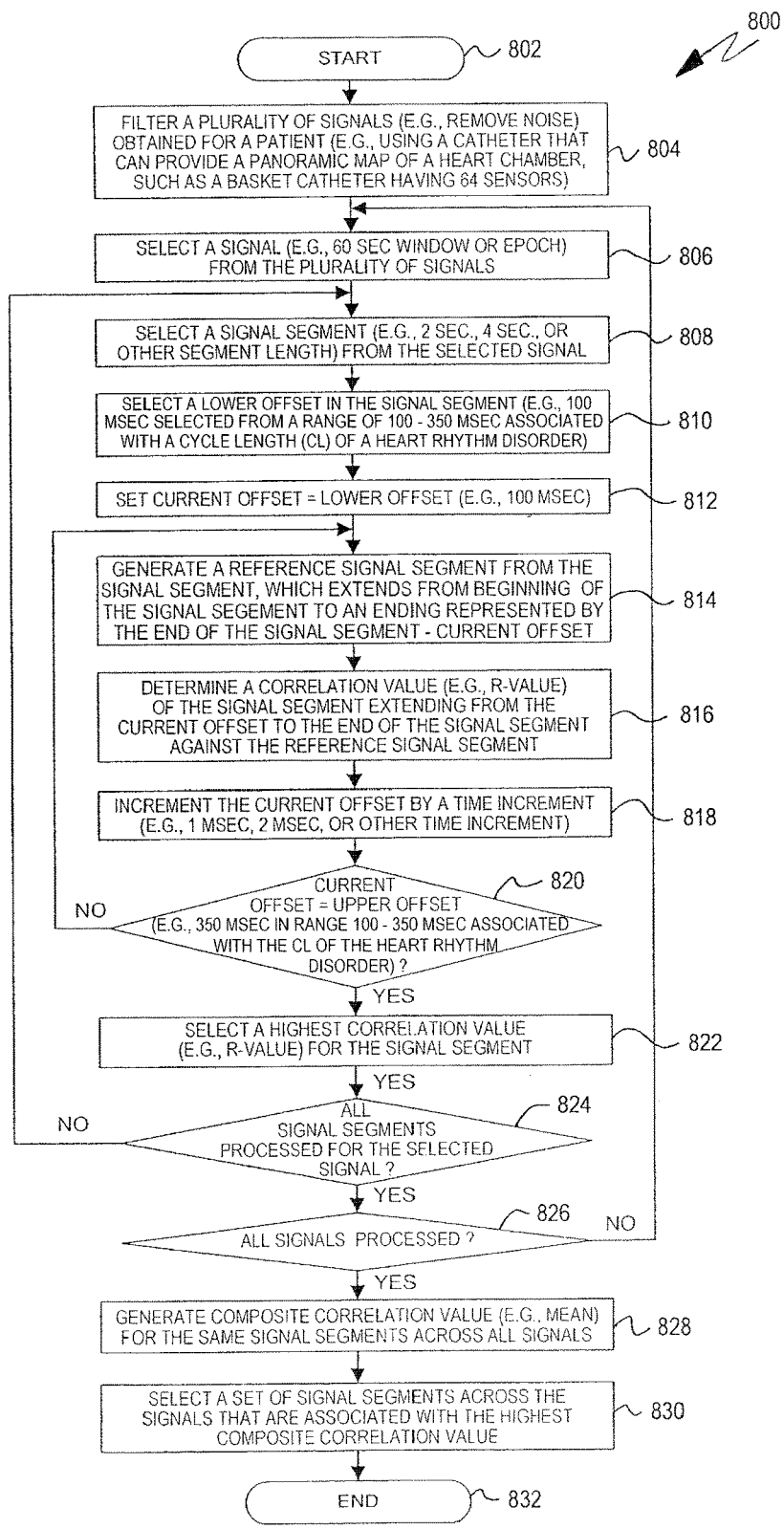
FIG. 8 is a flowchart that illustrates an example method of selecting signal segments for analysis of a biological rhythm disorder, such as heart rhythm disorder, according to a first embodiment.

FIG. 8 is a flowchart that illustrates an example method 800 of selecting signal segments for analysis of a biological rhythm disorder (e.g., heart rhythm disorder), according to a first embodiment. The example method 800 can be performed by the computing device 116 illustrated in FIG. 1.

More specifically, the example method 800 starts at operation 802 at which a plurality of signals is received or accessed by the computing device 116 via signal processing device 114 from the sensors disposed in the heart 120. The signals can be of a particular length, e.g., 60 seconds or longer. For example, the signals 202-206 are from sensors 102-106 of the catheter 101 disposed in the right atrium 122 of the heart 120, as illustrated in FIG. 1. In some embodiments or aspects, at least a portion of the signals from the sensors can be recorded by signal processing device 114 and then provided to computing device 116.

At operation 804, the plurality of received or accessed signals is filtered using one or more filtering methods. Filtering methods that can be used include, but are not limited to, QRS complex removal, median filtering, and frequency (bandpass) filtering. Other filtering methods can of course be used to reduce noise in the signal and increase signal quality. At operation 806, a signal is selected from the plurality of signals. As described herein, the selected signal can have a discrete length or can be epoch of a longer signal. At operation 808, a signal segment is selected from the selected signal. For example, the signal segment can be of a particular length (e.g., 2 seconds, 4 seconds, etc.). As described with reference to FIGS. 3-5, the signal segments can overlap at least partially.

At operation 810, a lower offset (e.g., 100 msec) in a range of offsets (e.g., 100 msec-350 msec) is selected in reference to the selected signal segment. At operation 812, a current offset is set to the lower offset. At operation 814, a reference signal segment is generated from the selected signal segment, which extends from the beginning of the selected signal segment to an ending represented by the end of the selected signal segment minus the current offset.

At operation 816, a correlation value (e.g., correlation coefficient (r)) is determined based on the selected signal segment extending from the current offset to the end of the selected signal segment, and based on the reference signal segment generated at operation 814, e.g., using the correlation calculation set forth in FIG. 9. At operation 818, the current offset is incremented by a time increment (e.g., 1 msec, 2 msec, or another time increment). At operation 820, a determination is made as to whether the current offset equals the upper offset (e.g., 350 msec) of the range of offsets (e.g., 100 msec-350 msec).

If it is determined that the current offset does not equal the upper offset at operation 820, the method 800 continues by performing the operations 814-820 again. However, if it is determined that current offset equals the upper offset at operation 820, the method 800 continues at operation 822 to select a highest correlation value (e.g., correlation coefficient (r)) for the selected signal segment.

In alternate embodiments, operations 808-820 can also be performed on the basis of offsets that are decremented. Specifically, the current offset at operation 812 can be set to the upper offset (e.g., 350 msec) in reference to the selected signal segment. At operation 818, the current offset can be decremented by a time decrement (e.g., 1 msec. 2 msec, or other time increment). Similarly, at operation 820 a determination can be made as to whether the current offset equals the lower offset (e.g., 100 msec).

At operation 824, a determination is made as to whether all signal segments of the selected signal were processed. If it is determined that all signal segments of the selected signal were not processed, the method 800 continues by performing the operations 808-824 again. However, if it is determined that all signal segments of the selected signal were processed at operation 824, the method 800 continues at operation 826. While operations 808-824 are illustrated in sequential order to facilitate understanding, it is noted that these operations can be performed contemporaneously or in a staggered manner for multiple or all signal segments among the signals.

At operation 826, a determination is made as to whether all signals were processed. If it is determined that all signals were not processed, the method 800 continues by performing the operations 806-826 for the next selected signal. However, if it is determined that all signals were processed at operation 826, the method 800 continues at operation 828 to generate a composite correlation value (e.g., sum, mean, SMR) for the same (approximately contemporaneous) signal segments across all of the processed signals.

It should be noted that the method 800 can be performed in connection with different selected range of offsets (e.g., 100 msec-350 msec, 300 msec-500 msec, 450 msec-1300 msec, or another range of offsets). At operations 810 and 820, the lower and upper offsets can thus correspond to the starting and ending offsets of the selected range of offsets, respectively.

At operation 830, a set of signal segments (approximately contemporaneous signal segments) that are associated with the highest composite correlation value out of a plurality of composite correlation values is selected. The selected signal segments can used to improve the time and accuracy of identifying a source of a heart rhythm disorder, as well as the time and accuracy in the targeting of the source of the heart rhythm disorder for treatment and elimination. For example, the selected signal segments can be processed as input signals by U.S. Pat. No. 8,165,666 to Briggs, et al., the subject matter of which is incorporated herein by reference in its entirety.

FIG. 9 illustrates an example correlation calculation 900 of a signal segment for a given time offset (e.g., 100 msec).

The correlation calculation 900 determines the correlation coefficient (r) as the summation of the product of two discrete data series, with each x or y representing a voltage element at each msec of the discrete data series having n elements. As illustrated, the correlation coefficients are normalized to a range −1 to 1. Specifically, x and y represent data series of equal length (size) based on the signal segment to be correlated as described with reference to FIGS. 6-8. If we let n be the length (msec) of the signal segment (e.g., n=2,000 for a signal segment of 2000 msec in length) and we let t be the time offset, then x will be populated by voltage elements starting from the beginning of the signal segment to n−t, and y will be populated by voltage elements starting from t in the signal segment to n. The $\bar{x}$ and $\bar{y}$ represent the mean values of the x and y data series, respectively. The x(i) and y(i) represent the $i^{th}$ element in the data series x and y, respectively. The example correlation calculation 900 determines the correlation coefficient (r) of the signal segment for the given time offset.

FIG. 10 illustrates an example table 1000 that summarizes highest correlation coefficients (r) for the signal segments 1002 (e.g., 2 msec-4 msec, 3 msec-5 msec signal, and 4 msec-6 msec segments) in each of the signals 202-206 in FIG. 2.

The table 1000 further illustrates a composite correlation coefficient 1004 of the highest correlation coefficients (r) for the same (approximately contemporaneous) signal segment 1002 (e.g., 2 msec-4 msec signal segment) among the different signals 202-206. The composite correlation coefficient 1004 can be a sum 1006 of the highest correlation coefficients (r), a mean 1008 of the highest correlation coefficients (r), or a square-mean-root (SMR) 1010 of the highest correlation coefficients (r), for the same signal segment 1002 (e.g., 2 msec-4 msec signal segment) among the signals 202-206. The calculation of the SMR 1010 is described in greater detail with reference to FIG. 11.

FIG. 11 illustrates an example calculation 1100 for the SMR 1010 of the highest correlation coefficients (r). Specifically, x represents an array of correlation coefficients (r) having a size of n. The $x_i$ represents the $i^{th}$ element of the x array. The example calculation 1100 determines a sum of the square root of each element i, normalized by dividing by n. The normalized sum is squared to determine the SMR. The SMR 1010 reduces the effect of a high correlation coefficient (r) of a certain signal segment with respect to more common correlation coefficients (r) of other signal segments in connection with the composite correlation coefficient 1004.

Figure 12:
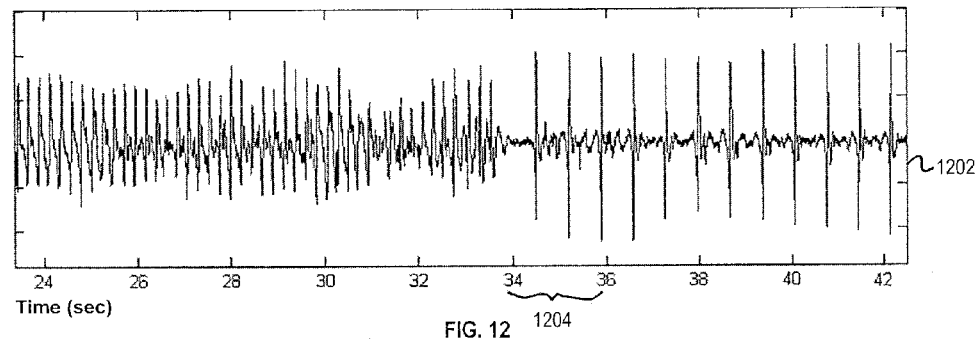
FIG. 12 illustrates an example signal of a complex heart rhythm disorder obtained in connection with an example sensor positioned at a sensed location in the heart of FIG. 1.

FIG. 12 illustrates an example signal 1202 of a complex heart rhythm disorder obtained in connection with an example sensor 102 positioned at a sensed location in the heart 120 of FIG. 1. In this example, the signal 1202 of the complex rhythm disorder represents an epoch (also a signal) of a sixty-second signal illustrated in FIG. 20, in order to show with clarity a transition (e.g., at about 34 seconds) from one rhythm to another rhythm associated with the complex heart rhythm disorder.

While only one signal 1202 is illustrated for clarity and brevity, it is noted that a plurality of signals can be provided by the catheter 101, e.g., 64 signals from corresponding sensors of a basket catheter can provide a panoramic view of the right atrium 122 of the heart 120, as described for example with reference to FIG. 2. As described herein, such signals are obtained approximately contemporaneously (e.g., at or about the same time).

As described with reference to FIGS. 2-5, the plurality of signals (including the signal 1202) can be similarly segmented using the computing device 116 into multiple signal segments having a segment length (e.g., two (2) seconds in length). Similarly, the signal segments can include multiple signals segments that overlap at least partially, such as for example, signals segments 24-26 seconds, 25-27 seconds, 26-28 seconds, . . . , 39-41 seconds, and 40-42 seconds. It is noted that a different segment length (e.g., four (4) seconds) can be selected for segmentation of the signal 1202 based on its overall length, for example.

In accordance with this example, each group of approximately contemporaneous signal segments (e.g., signal segments having approximately the same start time) is successively processed among the plurality of signals. With reference to signal 1202, each of the signal segments from the beginning of the signal 1202 and including the signal segment 1204 (e.g., 34-36 seconds) is thus successively correlated with itself (e.g., using correlation calculation of FIG. 9) over a first selected range of the time offsets to determine a plurality of correlation coefficients (r) at the plurality of offsets in each of the signal segments. For each signal segment of the signal 1202, the signal segments of the plurality of signals that are approximately contemporaneous (e.g., having approximately the same start time) are similarly correlated (e.g., using correlation calculation of FIG. 9), thus forming a group of signal segments (e.g., the group including signal segments having approximately the same start time).

It is noted that the first selected range of time offsets is associated with a cycle length of a biological rhythm disorder (e.g., heart rhythm disorder). As described hereinbefore, the first selected range can be 100 msec-350 msec. The foregoing correlation over the first selected range of offsets is repeated for each successive group of approximately contemporaneous signal segments among the plurality of signals.

A highest correlation coefficient (r) is selected for each of the approximately contemporaneous signal segments in each group. Moreover, a first composite correlation value (e.g., mean correlation coefficient) is generated for the same signal segments among the plurality of signals (e.g., signal segments of each group with approximately the same start time across the plurality of signals). The first selected range (e.g., 100 msec-350 msec) and a mean offset of signal segments can be stored in association with the first composite correlation value. Thereafter, the first composite correlation value is compared to a selected threshold (e.g., 0.3).

If the first composite correlation coefficient is greater than the selected threshold for the group of contemporaneous signal segments, then a next successive group of signal segments is correlated as described hereinabove using the first selected range, and a first composite correlation value (e.g., mean correlation coefficient) is generated for this successive group of signal segments.

However, if the first composite correlation coefficient is less than or equal to the selected threshold (e.g., 0.3), then the signal segments of this group are re-correlated using a second selected range of 300 msec-500 msec. A second composite correlation value (e.g., mean correlation coefficient) is generated for this group. The second selected range (e.g., 300 msec-500 msec) and a mean offset of signal segments can be stored in association with the second composite correlation value. Thereafter, the second composite correlation coefficient is compared to the selected threshold.

If the second composite correlation coefficient is greater than the selected threshold, then a next successive group of signal segments is correlated as described hereinabove (e.g., using the first selected range of 100 msec-350 msec), and a composite correlation value (e.g., mean correlation coefficient) is generated for the next successive group. However, if the second composite correlation coefficient is less than or equal to the selected threshold, then the signal segments of this group are re-correlated using a third selected range of 450 msec-1300 msec. A third composite correlation value (e.g., mean correlation coefficient) is generated for this group. The third selected range (e.g., 450 msec-1300 msec) and a mean offset of signal segments can be stored in association with the third composite correlation value. Thereafter, the third composite correlation coefficient is compared to the selected threshold. It should be noted that in some embodiments, the second and third composite correlation coefficients are generated even if the first and/or second composite correlation coefficient is above the selected threshold.

If the third composite correlation coefficient is greater than the selected threshold, then a next successive group of signal segments is correlated as described hereinabove (e.g., using the first selected range of 100 msec-350 msec), and a composite correlation value (e.g., mean correlation coefficient) is generated for the next successive group. However, if the third composite correlation coefficient is less than or equal to the selected threshold, then a "do not use" indication is stored in association with this group of signal segments, e.g., the group is not to be used because there is limited consistency among the approximately contemporaneous signals segments of the plurality of signals. It should be noted that in some embodiments, more than three composite correlation coefficients can be calculated using additional or different selected ranges of offsets.

The remaining groups of approximately contemporaneous signal segments among of the plurality of signals are processed accordingly, e.g., using ranges of offsets (e.g., 100 msec-350 msec; 300-500 msec; and 450-1300 msec). In the example signal 1202, the signal segments up to about 34 seconds are similar to the signal segments illustrated in FIGS. 2-5. It can be expected that the first composite correlation value associated with the first selected range of offsets (100 msec-350 msec) will be greater than the selected threshold for the signal segments in the groups up to about 34 seconds, and less than the selected threshold for the signals segments at and after about 34 seconds. The processing of these signal segments in accordance with the different ranges of offsets is described in greater detail below with reference to FIGS. 13-18.

Figure 13:
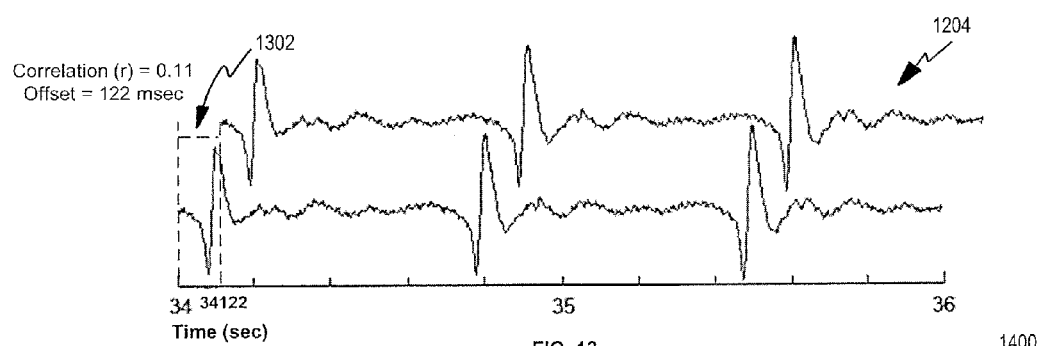
FIG. 13 illustrates an example time shift (or offset) in the signal segment of the signal illustrated in FIG. 12 according to the first selected range of offsets.

FIG. 13 illustrates an example time shift (or offset) 1302 in the signal segment 1204 of the signal 1202 illustrated in FIG. 12 according to the first selected range of offsets.

As described previously, there are 250 time offsets in accordance with the first selected range of offsets (e.g., 100 msec-350 msec). While not shown, a correlation coefficient (r) is calculated for each of the time offsets in the range 100 msec-350 msec using the example correlation calculation of FIG. 9.

For the signal segment 1204, the maximum correlation coefficient (r)=0.11 is obtained at the offset of 122 msec. It is noted that a different correlation method or technique can be used to correlate (e.g., auto-correlate) the example signal segment 1204 with itself. It is noted that the maximum correlation coefficient for signal segment 1204 is below the threshold value (e.g., 0.3), as described with reference to FIG. 12.

Figure 14:
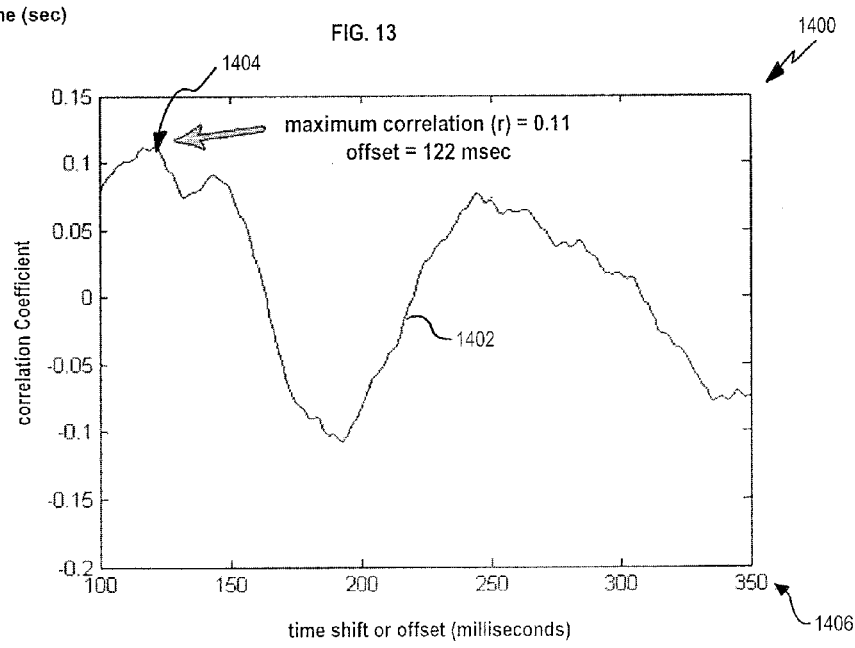
FIG. 14 illustrates an example graph showing a curve of the correlation coefficients (r) determined for the time offsets in accordance with the first selected range of offsets in the signal segment of the signal illustrated in FIG. 12.

FIG. 14 illustrates an example graph 1400 showing a curve 1402 of the correlation coefficients (r) determined for the time offsets in accordance with the first selected range of offsets 1406 in the signal segment 1204 of the signal 1202 illustrated in FIG. 12.

As illustrated in FIG. 14, the correlation coefficients are between −0.10 to 0.11 in the first selected range of time offsets 1406 (e.g., between 100 msec-350 msec), with the maximum correlation coefficient (r)=0.11 occurring at the time offset of 122 msec.

It should be noted that a similar curve can be generated to illustrate the correlation coefficients (r) determined for the time offsets in the first selected range of offsets for the approximately contemporaneous signals segments of the other signals.

Figure 15:
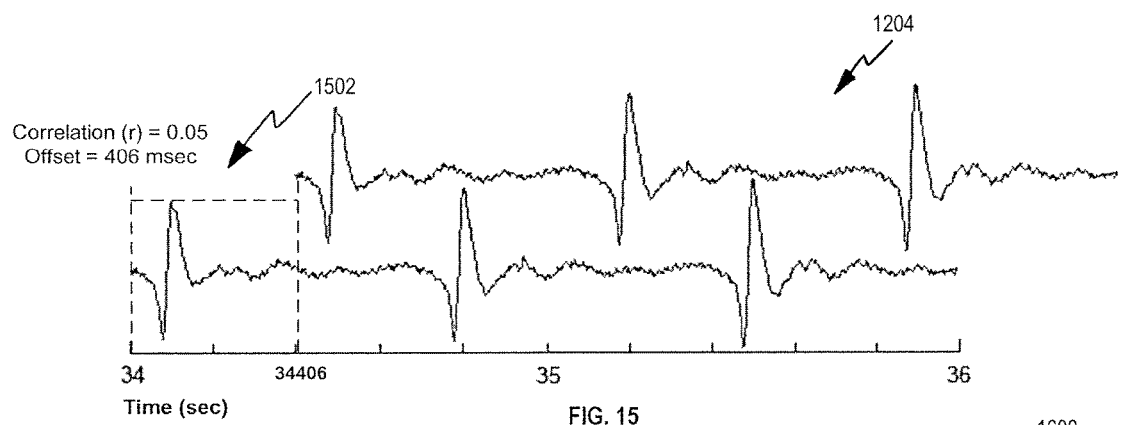
FIG. 15 illustrates an example time shift (or offset) in the signal segment of the signal illustrated in FIG. 12 according to the second selected range of offsets.

FIG. 15 illustrates an example time shift (or offset) 1502 in the signal segment 1204 of the signal 1202 illustrated in FIG. 12 according to the second selected range of offsets.

There are 200 time offsets in accordance with the second selected range of offsets (e.g., 300 msec-500 msec). While not shown, a correlation coefficient (r) is calculated for each of the time offsets in the range 300 msec-500 msec using the example correlation calculation of FIG. 9.

For the signal segment 1204, the maximum correlation coefficient (r)=0.05 is obtained at the offset of 406 msec. It is noted that a different correlation method or technique can be used to correlate (e.g., auto-correlate) the example signal segment 1204 with itself. It is noted that the maximum correlation coefficient for signal segment 1204 is also below the threshold value (e.g., 0.3), as described with reference to FIG. 12.

Figure 16:
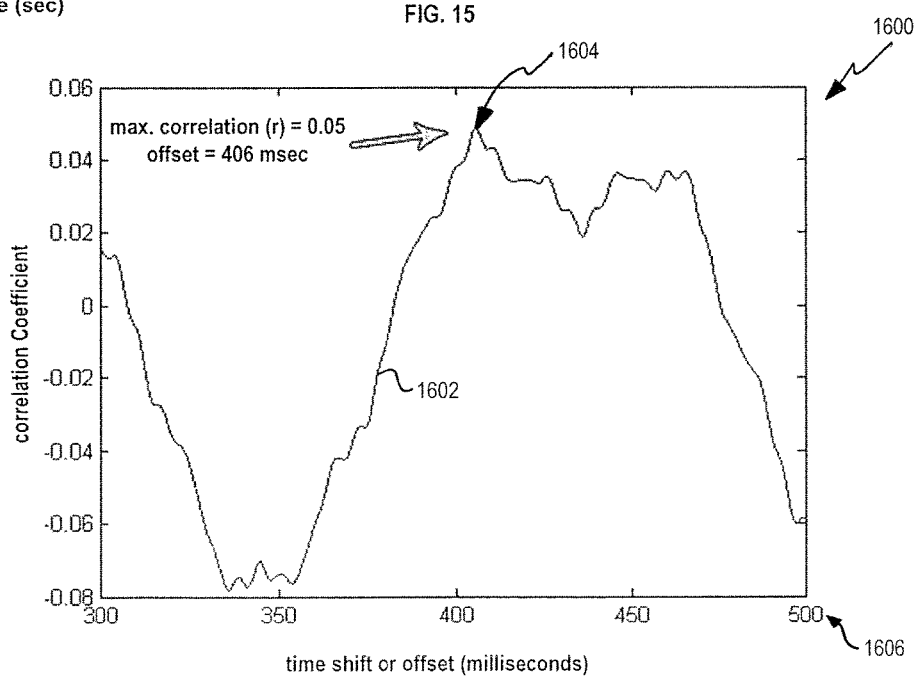
FIG. 16 illustrates an example graph showing a curve of the correlation coefficients (r) determined for the time offsets in accordance with the second selected range of offsets in the signal segment of the signal illustrated in FIG. 12.

FIG. 16 illustrates an example graph 1600 showing a curve 1602 of the correlation coefficients (r) determined for the time offsets in accordance with the second selected range of offsets 1606 in the signal segment 1204 of the signal 1202 illustrated in FIG. 12.

As illustrated in FIG. 16, the correlation coefficients are between −0.08 to 0.05 in the second selected range of time offsets 1606 (e.g., between 300 msec-500 msec), with the maximum correlation coefficient (r)=0.05 occurring at the time offset of 406 msec.

It should be noted that a similar curve can be generated to illustrate the correlation coefficients (r) determined for the time offsets in the second selected range of offsets for the approximately contemporaneous signals segments of the other signals.

Figure 17:
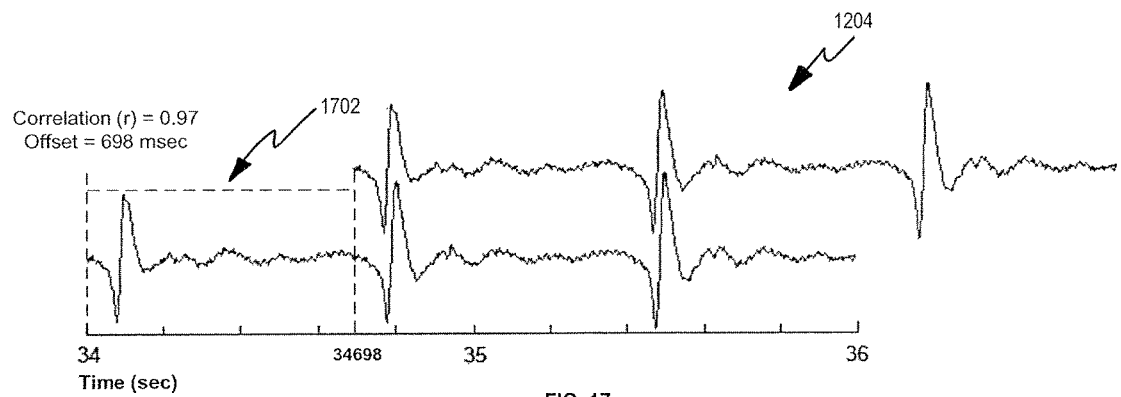
FIG. 17 illustrates an example time shift (or offset) in the signal segment of the signal illustrated in FIG. 12 according to the third selected range of offsets.

FIG. 17 illustrates an example time shift (or offset) 1702 in the signal segment 1204 of the signal 1202 illustrated in FIG. 12 according to the third selected range of offsets.

There are 750 time offsets in accordance with the third selected range of offsets (e.g., 450 msec-1300 msec). While not shown, a correlation coefficient (r) is calculated for each of the time offsets in the range 450 msec-1300 msec using the example correlation calculation of FIG. 9.

For the signal segment 1204, the maximum correlation coefficient (r)=0.97 is obtained at the offset of 698 msec. It is noted that a different correlation method or technique can be used to correlate (e.g., auto-correlate) the example signal segment 1204 with itself. It is noted that the maximum correlation coefficient for signal segment 1204 is above the threshold value (e.g., 0.3), as described with reference to FIG. 12.

Figure 18:
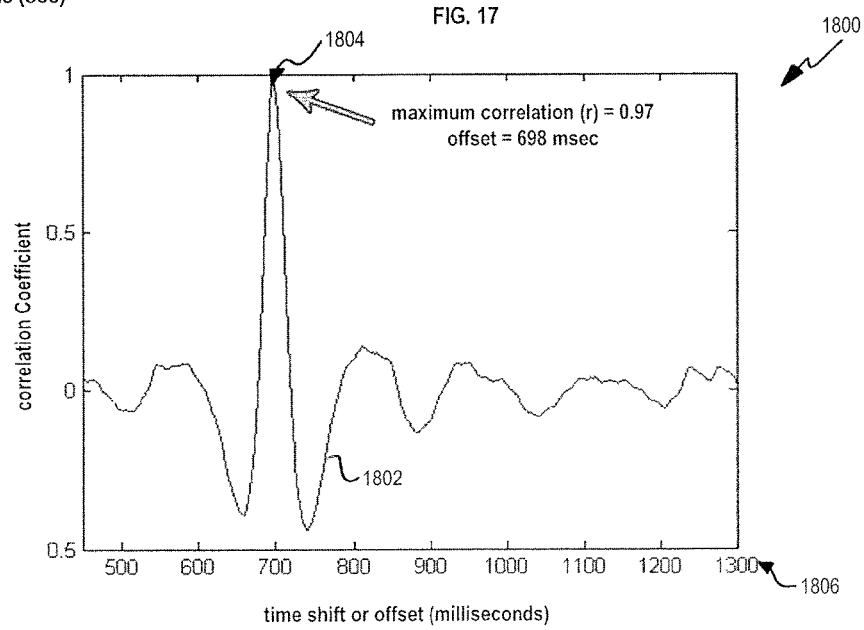
FIG. 18 illustrates an example graph showing a curve of the correlation coefficients (r) determined for the time offsets in accordance with the third selected range of offsets in the signal segment of the signal illustrated in FIG. 12.

FIG. 18 illustrates an example graph 1800 showing a curve 1802 of the correlation coefficients (r) determined for the time offsets in accordance with the third selected range of offsets 1806 in the signal segment 1204 of the signal 1202 illustrated in FIG. 12.

As illustrated in FIG. 18, the correlation coefficients are between −0.45 to 0.97 in the third selected range of time offsets 1806 (e.g., between 450 msec-1300 msec), with the maximum correlation coefficient (r)=0.97 occurring at the time offset of 698 msec.

It should be noted that a similar curve can be generated to illustrate the correlation coefficients (r) determined for the time offsets in the second selected range of offsets for the approximately contemporaneous signals segments of the other signals.

Figure 19:
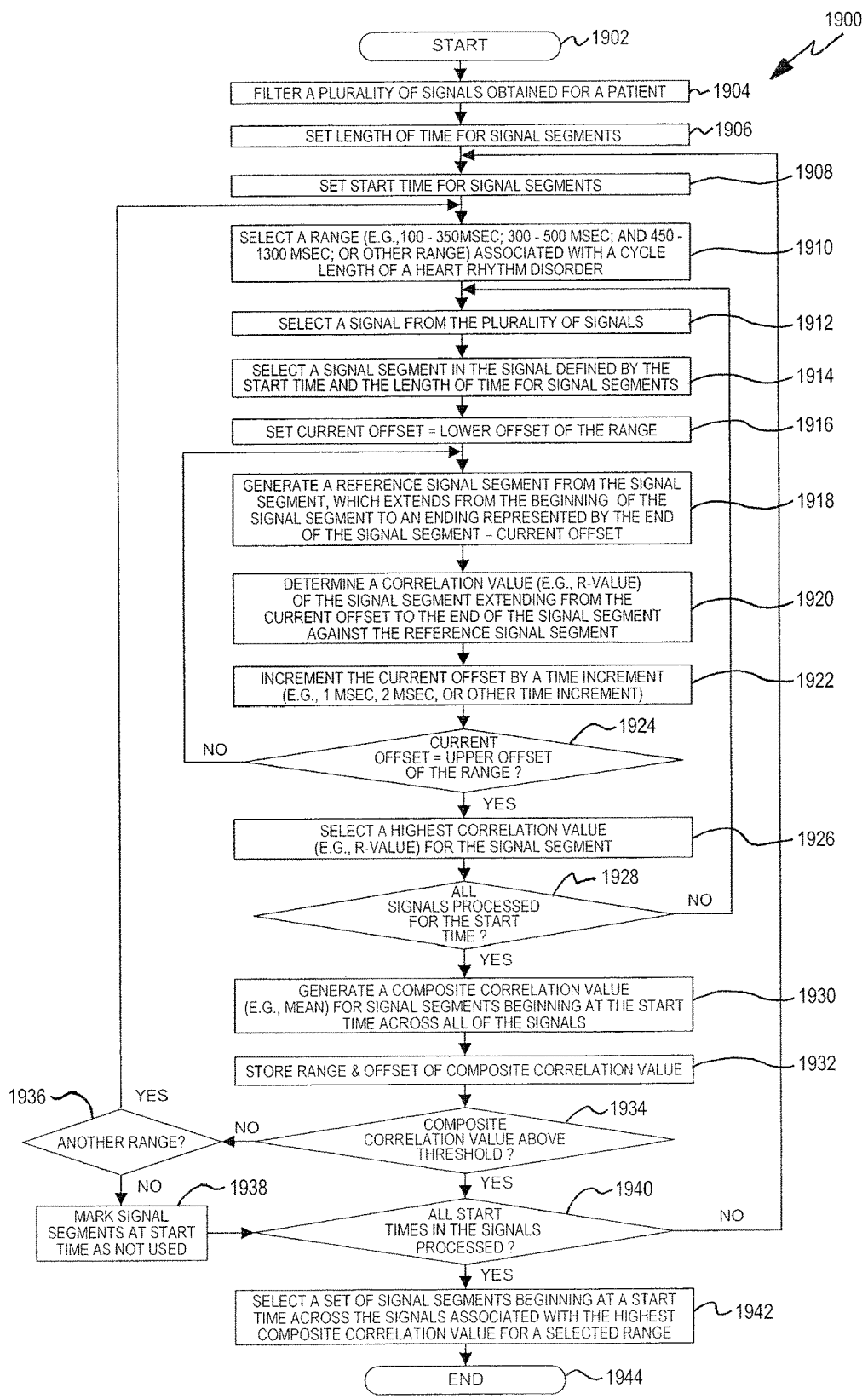
FIG. 19 is a flowchart that illustrates an example method of selecting signal segments for analysis of a biological rhythm disorder, such as a heart rhythm disorder, according to a second embodiment.

FIG. 19 is a flowchart that illustrates an example method 1900 of selecting signal segments for analysis of a biological rhythm disorder (e.g., heart rhythm disorder), according to a second embodiment. The example method 1900 can be performed by the computing device 116 illustrated in FIG. 1.

More specifically, the example method 1900 starts at operation 1902 at which a plurality of signals is received or accessed by the computing device 116 via signal processing device 114 from the sensors disposed in the heart 120. The signals can be of a particular length, e.g., 60 seconds or longer. In some embodiments or aspects, at least a portion of the signals from the sensors can be recorded by signal processing device 114 and then provided to computing device 116.

At operation 1904, the plurality of received or accessed signals is filtered using one or more filtering methods. Filtering methods that can be used include, but are not limited to, QRS complex removal, median filtering, and frequency (bandpass) filtering. Other filtering methods can of course be used to reduce noise in the signal and increase signal quality.

At operation 1906, a length of time for signals segments in the plurality of signals is set. As described herein, the length of time can be 2 seconds, 4 seconds, or another length of time. At operation 1908, a start time for signal segments is set in order to select approximately contemporaneous signal segments (e.g., signal segments starting at approximately the same start time) among the plurality of signals. Initially, the start time can be set to the beginning of the signals (e.g., start time of zero (0)). Thereafter, the start time can be incremented by a time increment (e.g., one (1) second) for each iteration of the operations 1908-1940 in order to select successive signal segments in the plurality of signals.

At operation 1910, a range of offsets associated with a cycle length of a heart rhythm disorder is selected. As described with reference to FIGS. 12-18, the first range (e.g., 100 msec-350 msec) is selected initially. As will be described hereinbelow, other ranges that can be selected include the second range (e.g., 300 msec-500 msec) and the third range (e.g., 450 msec-1300 msec). Other ranges can be defined.

At operation 1912, a signal is selected from the plurality of signals. As described herein, the selected signal can have a discrete length or can be epoch of a longer signal. At operation 1914, a signal segment is selected from the selected signal. The selected signal segment is defined by the start time and the length of time.

At operation 1916, a current offset is set to the lower offset of the range of offsets selected at operation 1910. At operation 1918, a reference signal segment is generated from the selected signal segment, which extends from the beginning of the selected signal segment to an ending represented by the end of the selected signal segment minus the current offset.

At operation 1920, a correlation value (e.g., correlation coefficient (r)) is determined based on the selected signal segment extending from the current offset to the end of the selected signal segment, and based on the reference signal segment generated at operation 918, e.g., using the correlation calculation set forth in FIG. 9. At operation 1922, the current offset is incremented by a time increment (e.g., 1 msec, 2 msec, or another time increment). At operation 1924, a determination is made as to whether the current offset equals the upper offset of the selected range (e.g., 350 msec for the first selected range).

If it is determined that the current offset does not equal the upper offset at operation 1924, the method 1900 continues by performing the operations 1918-1924 again. However, if it is determined that current offset equals the upper offset at operation 1924, the method 1900 continues at operation 1926 to select a highest correlation value (e.g., correlation coefficient (r)) for the selected signal segment.

In alternate embodiments, operations 1914-1924 can also be performed on the basis of offsets that are decremented. Specifically, the current offset at operation 1916 can be set to the upper offset in reference to the selected signal segment. At operation 1922, the current offset can be decremented by a time decrement (e.g., 1 msec. 2 msec, or other time increment). Similarly, at operation 1924 a determination can be made as to whether the current offset equals the lower offset of the selected range (e.g., 100 msec for the first selected range).

At operation 1928, a determination is made as to whether the approximately contemporaneous signals segments of all signals were processed (e.g., all signals processed for signal segments having the selected segment start time). If it is determined that all signals were not processed, the method 1900 continues by performing the operations 1912-1928 again. However, if it is determined that all signals were processed at operation 1928, the method 1900 continues at operation 1930. While operations 1912-1928 are illustrated in sequential order to facilitate understanding, it is noted that these operations can be performed contemporaneously or in a staggered manner for different groups of approximately contemporaneous signal segments among the signals.

At operation 1930, a composite correlation value (e.g., sum, mean, SMR) is generated for the same (approximately contemporaneous) signal segments across all of the signals. At operation 1932, the selected range and a mean offset (e.g., mean of offsets of approximately contemporaneous signals segments) is stored in association with the composite correlation value.

At operation 1934, a determination is made as to whether the composite correlation value is above the threshold (e.g., 0.3). If at operation 1934 it is determined that the composite correlation value is below or equal to the threshold, the method 1900 continues at operation 1936, where a determination is made as to whether another range of offsets is selectable. If so, the method 1900 continues at operation 1910 where another range of offsets is selected and operations 1910-1934 repeated. The selected range of offsets can be the second range of offsets (e.g., 300 msec-500 msec). As described hereinabove, three defined ranges of offsets can be selected at operation 1936 (e.g., 100 msec-350 msec; 300 msec-500 msec; and 450 msec-1300 msec). It is noted that other ranges can be defined and thus selected at operation 1936. If another range of offsets is not selectable, then the signal segments are marked as not used at operation 1938, and the method 1900 continues at operation 1940.

If at operation 1934 it is determined that the composite correlation value is above the threshold, the method 1900 continues at operation 1940, where a determination is made as to whether all signal segments have been processed in the signals. More specifically, it is determined whether all start times for signal segments in the plurality of signals have been processed. If not, the method 1900 performs operations 1908-1940 for the additional signal segments in the plurality of signals, i.e., setting a next successive start time for approximately contemporaneous signal segments not yet processed in the plurality of signals. After the determination at operation 1940 that all signal segments in the plurality of signals have been processed, the method 1900 continues at operation 1942. At operation 1942, a set of approximately contemporaneous segments that are associated with the highest composite correlation value for a selected range of offsets is selected. The method 1900 ends at operation 1944.

The selected signal segments can used to improve the time and accuracy of identifying a source of a heart rhythm disorder, as well as the time and accuracy in the targeting of the source of the heart rhythm disorder for treatment and elimination. For example, the selected signal segments can be processed as input signals by U.S. Pat. No. 8,165,666 to Briggs, et al., the subject matter of which is incorporated herein by reference in its entirety.

Figure 20:
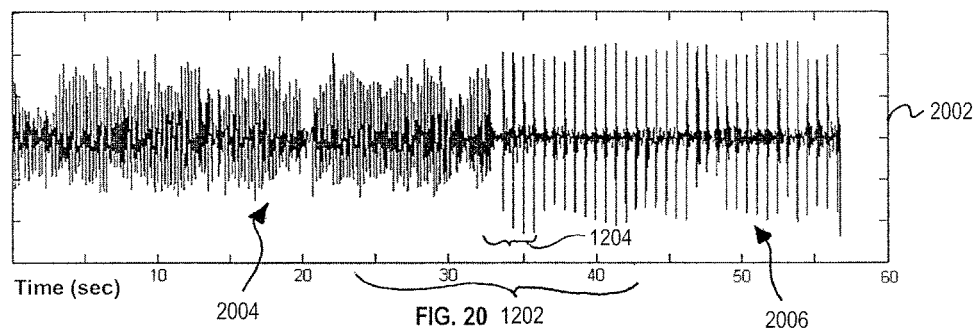
FIG. 20 illustrates an example signal of a complex heart rhythm disorder obtained in connection with an example sensor positioned at a sensed location in the heart of FIG. 1.

FIG. 20 illustrates an example signal 2002 of a complex heart rhythm disorder obtained in connection with an example sensor 102 positioned at a sensed location in the heart 120 of FIG. 1. The signal 2002 a sixty-seconds and includes the epoch or signal 1202 illustrated in FIG. 12. As illustrated, rhythm of a section 2004 transitions (e.g., at about 34 seconds) to another rhythm of a section 2006.

Figure 21:
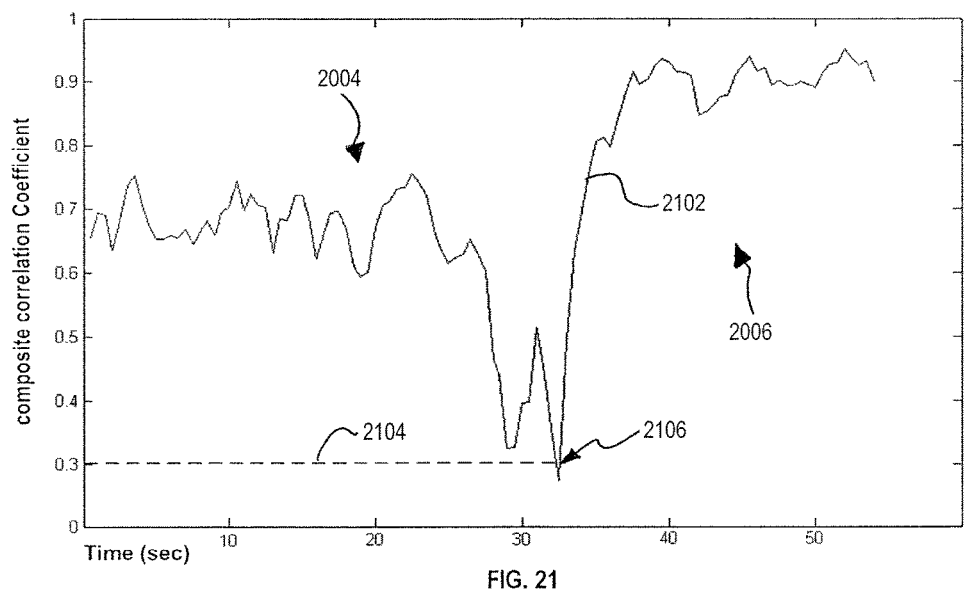
FIG. 21 illustrates an example curve of the composite correlation coefficients associated with the segments of a plurality of signals including the signal illustrated in FIG. 20.

FIG. 21 illustrates an example curve 2102 of the composite correlation coefficients associated with the segments of a plurality of signals including the signal 2002. The composite correlation coefficients are associated with overlapping signal segments of two-second length obtained every second among the plurality of signals including signal 2002, e.g., 0-2 second, 1-3 seconds, . . . , 32-34 seconds, . . . , 57-59 seconds, and 58-60 seconds.

During the section 2004, the composite correlation coefficients of the approximately contemporaneous signals segments in the plurality of signals vary between about 0.58 and about 0.76. At approximately 2106 (e.g., signal segments 32-34 seconds) in the plurality of signals, a composite correlation coefficient drops below a threshold 2104 associated with a threshold value (e.g., 0.3). During the section 2006, the composite correlation coefficients of the approximately contemporaneous signals segments in the plurality of signals vary between about 0.8 and about 0.96.

As illustrated, there is consistency of periodicity among the plurality of signals during section 2004, significant drop off in periodic consistently at 2106, and resumption in consistency of periodicity among the plurality of signals during section 2006. Consistency of periodicity is lower during section 2004 than consistency of periodicity during section 2006. The less consistent rhythm associated with the heart rhythm disorder transitions to a more consistent rhythm. In this example, the more consistent rhythm is a normal sinus rhythm. More specifically, there is cessation of the rhythm associated with the heart rhythm disorder and conversion to a normal sinus rhythm.

Figure 22:
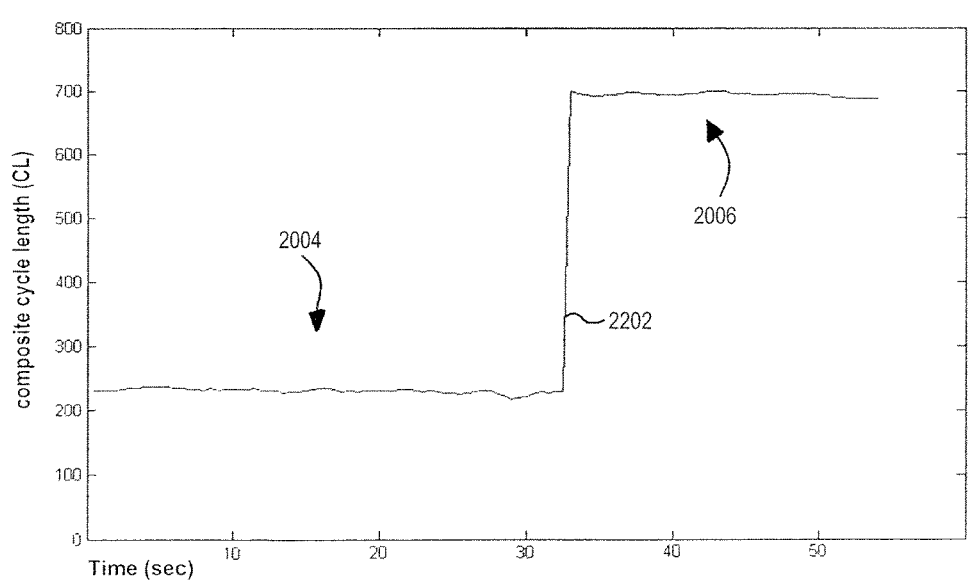
FIG. 22 illustrates an example curve of the composite offset associated with cycle length (CL) of the heart rhythm disorder accounting for the contemporaneous segments of the plurality of signals including the signal illustrated in FIG. 20.

FIG. 22 illustrates an example curve 2202 of the composite offset associated with cycle length (CL) of the heart rhythm disorder accounting for the contemporaneous segments of the plurality of signals including the signal 2002.

During section 2004, the composite offset associated with the CL of the heart rhythm disorder is approximately 220 msec, which falls in the first selectable range of offsets (e.g., 100 msec to 350 msec). During section 2006, the composite offset associated with normal sinus rhythm is approximately 700 msec, which is in the third selectable range of offsets (e.g., 450 msec to 1300 msec).

In accordance with the second embodiment, the use of selectable ranges of offsets enables detection of one or more rhythms that are associated with a heart rhythm disorder, as well as transitions among these rhythms. The transitions can include not only transitions among abnormal rhythms (e.g., from AF to AT, and others), but can also include transitions from abnormal rhythms (e.g., AF, AT, and others) to a normal sinus rhythm. This enables the selection (e.g., using ranges of offsets) of approximately contemporaneous signal segments (of the plurality of signals) in connection with a particular rhythm associated with the heart rhythm disorder for further analysis.

Figure 23:
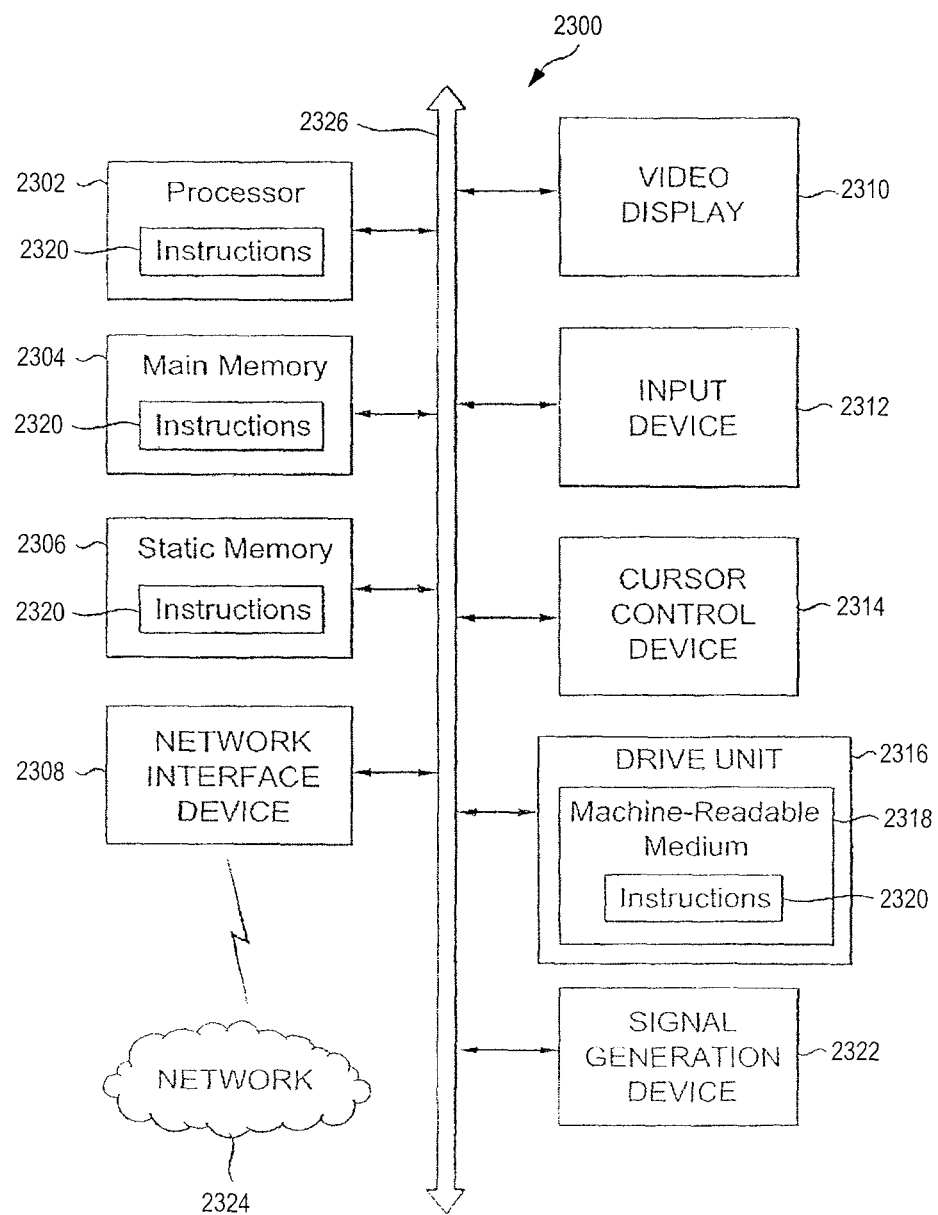
FIG. 23 is a block diagram of an illustrative embodiment of a general computer system.

FIG. 23 is a block diagram of an illustrative embodiment of a general computer system 1200. The computer system 2300 can be the signal processing device 114 and the computing device 116 of FIG. 1. The computer system 1200 can include a set of instructions that can be executed to cause the computer system 2300 to perform any one or more of the methods or computer based functions disclosed herein. The computer system 2300, or any portion thereof, may operate as a standalone device or may be connected, e.g., using a network or other connection, to other computer systems or peripheral devices. For example, the computer system 1200 may be operatively connected to the signal processing device 114.

The computer system 2300 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 2300 is illustrated, the term "system" shall also be taken to include any collection of systems or sub-systems that individually or jointly execute a set, or multiple sets, of instructions to perform one or more computer functions.

As illustrated in FIG. 23, the computer system 2300 may include a processor 2302, e.g., a central processing unit (CPU), a graphics-processing unit (GPU), or both. Moreover, the computer system 2300 may include a main memory 2304 and a static memory 2306 that can communicate with each other via a bus 2326. As illustrated, the computer system 2300 may further include a video display unit 2310, such as a liquid crystal display (LCD), an organic light emitting diode (OLED), a flat panel display, a solid state display, or a cathode ray tube (CRT). Additionally, the computer system 2300 may include an input device 2312, such as a keyboard, and a cursor control device 2314, such as a mouse. The computer system 2300 can also include a disk drive unit 2316, a signal generation device 2322, such as a speaker or remote control, and a network interface device 2308.

In a particular embodiment or aspect, as depicted in FIG. 23, the disk drive unit 2316 may include a computer-readable medium 2318 in which one or more sets of instructions 2320, e.g., software, can be embedded. Further, the instructions 2320 may embody one or more of the methods or logic as described herein. In a particular embodiment or aspect, the instructions 2320 may reside completely, or at least partially, within the main memory 2304, the static memory 2306, and/or within the processor 2302 during execution by the computer system 1200. The main memory 2304 and the processor 2302 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computer systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computer system processing can be constructed to implement one or more of the methods or functionality as described herein.

It is also contemplated that a computer-readable medium includes instructions 2320 or receives and executes instructions 2320 responsive to a propagated signal, so that a device connected to a network 2324 can communicate voice, video or data over the network 2324. Further, the instructions 2320 may be transmitted or received over the network 2324 via the network interface device 2308.

While the computer-readable medium is illustrated to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, system and method to reconstruct cardiac activation information have been described. Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects illustrated. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

The invention claimed is:

1. A method of selecting signal segments of multiple cardiac signals, the method comprising:
   correlating, using a processing device, a signal segment in at least one first cardiac signal to the signal segment itself as shifted by a plurality of time offsets to determine a highest correlation coefficient associated with periodicity of the signal segment in the at least one first cardiac signal;
   correlating, using the processing device, a signal segment in at least one second cardiac signal to the signal segment itself as shifted by the plurality of time offsets to determine a highest correlation coefficient associated with periodicity of the signal segment in the at least one second cardiac signal;
   repeating, using the processing device, the correlating for additional signal segments in the at least one first cardiac signal and additional signal segments in the at least one second cardiac signal to determine a highest correlation coefficient associated with periodicity of each of the additional signal segments;
   generating, using the processing device, a plurality of composite correlation coefficients using highest correlation coefficients for the signal segments of the at least one first cardiac signal and the signal segments of the at least one second cardiac signal, each of the plurality of composite correlation coefficients associated with signal segments of the at least one first cardiac signal that are approximately contemporaneous with signal segments of the at least one second cardiac signal; and
   selecting, using the processing device, a set of signal segments including at least one signal segment from the at least one first cardiac signal and at least one signal segment from the at least one second cardiac signal, the set of signal segments being associated with a highest composite correlation coefficient from the plurality of composite correlation coefficients.

2. The method of claim 1, further comprising filtering the at least one first cardiac signal and the at least one second cardiac signal.

3. The method of claim 1, wherein the plurality of signal segments in the at least one first cardiac signal overlap at least partially.

4. The method of claim 1, wherein the plurality of signal segments in the at least one second cardiac signal overlap at least partially.

5. The method of claim 1, wherein each signal segment of the plurality of signal segments in the at least one first cardiac signal and the plurality of signal segments in the at least one second cardiac signal is of a predetermined segment length.

6. The method of claim 5, wherein the predetermined segment length is one of two seconds and four seconds in length.

7. The method of claim 1, wherein the plurality of time offsets is in a range of 100 msec to 350 msec.

8. The method of claim 1, wherein correlating a first signal segment in a first cardiac signal at a plurality of time offsets comprises:
   generating a first reference segment from the first signal segment, the first reference segment extending from a beginning of the first signal segment to an ending represented by an end of the first signal segment minus a first time offset;
   determining a first correlation coefficient of the first signal segment that extends from the first time offset in the first signal segment to the end of the first signal segment against the first reference segment;
   generating a second reference segment from the first signal segment, the second reference segment extending from a beginning of the first signal segment to an ending represented by the end of the first signal segment minus a second time offset;
   determining a second correlation coefficient of the first signal segment that extends from the second time offset in the first signal segment to the end of the first signal segment against the second reference segment; and
   selecting the highest correlation coefficient for the first cardiac signal among the first correlation coefficient and the second correlation coefficient.

9. The method of claim 8, wherein correlating a first signal segment in a second cardiac signal at a plurality of time offsets comprises:
   generating a first reference segment from the first signal segment, the first reference segment extending from a beginning of the first signal segment to an ending represented by an end of the first signal segment minus a first time offset;
   determining a first correlation coefficient of the first signal segment that extends from the first time offset in the first signal segment to the end of the first signal segment against the first reference segment;
   generating a second reference segment from the first signal segment, the second reference segment extending from a beginning of the first signal segment to an ending represented by the end of the first signal segment minus a second offset;
   determining a second correlation coefficient of the first signal segment that extends from the second time offset in the first signal segment to the end of the first signal segment against the second reference segment; and
   selecting the highest correlation coefficient for the second cardiac signal among the first correlation coefficient and the second correlation coefficient.

10. The method of claim 9, wherein generating a plurality of composite correlation coefficients comprises computing a sum of the highest correlation coefficient for the first cardiac signal and the highest correlation coefficient for the second cardiac signal.

11. The method of claim 9, wherein generating a plurality of composite correlation coefficients comprises computing a mean of the highest correlation coefficient for the first cardiac signal and the highest correlation coefficient for the second cardiac signal.

12. The method of claim 9, wherein generating a plurality of composite correlation coefficients comprises computing a square-mean-root of the highest correlation coefficient for the first cardiac signal and the highest correlation coefficient for the second cardiac signal.

13. The method of claim 1, wherein the plurality of composite correlation coefficients are generated using one of a sum, a mean and a square-mean-root of the highest correlation coefficients for the signal segments of the at least one first cardiac signal and the signal segments of the at least one second cardiac signal.

14. The method of claim 1, wherein the method further comprises processing the set of signal segments to determine a source of a cardiac rhythm disorder.

15. A system to select signal segments of multiple cardiac signals, the system comprising:
 a processing device; and
 a memory device to store instructions that, when executed by the processing device, cause the processing device to perform operations comprising:
  correlating a signal segment in at least one first cardiac signal to the signal segment itself as shifted by a plurality of time offsets to determine a highest correlation coefficient associated with periodicity of the signal segment in the at least one first cardiac signal;
  correlating a signal segment in at least one second cardiac signal to the signal segment itself as shifted by the plurality of time offsets to determine a highest correlation coefficient associated with periodicity of the signal segment in the at least one second cardiac signal;
  repeating the correlating for additional signal segments in the at least one first cardiac signal and additional signal segments in the at least one second cardiac signal to determine a highest correlation coefficient associated with periodicity of each of the additional signal segments;
  generating a plurality of composite correlation coefficients using highest correlation coefficients for the signal segments of the at least one first cardiac signal and the signal segments of the at least one second cardiac signal, each of the plurality of composite correlation coefficients associated with signal segments of the at least one first cardiac signal that are approximately contemporaneous with signal segments of the at least one second cardiac signal; and
  selecting a set of signal segments including at least one signal segment from the at least one first cardiac signal and at least one signal segment from the at least one second cardiac signal, the set of signal segments being associated with a highest composite correlation coefficient from the plurality of composite correlation coefficients.

16. The system of claim 15, wherein the operations further comprise filtering the at least one first cardiac signal and the at least one second cardiac signal.

17. The system of claim 15, wherein the plurality of signal segments in the at least one first cardiac signal overlap at least partially.

18. The system of claim 15, wherein the plurality of signal segments in the at least one second cardiac signal overlap at least partially.

19. The system of claim 15, wherein each signal segment of the plurality of signal segments in the at least one first cardiac signal and the plurality of signal segments in the at least one second cardiac signal is of a predetermined segment length.

20. The system of claim 19, wherein the predetermined segment length is one of two seconds and four seconds in length.

21. The system of claim 15, wherein the plurality of time offsets is in a range of 100 msec to 350 msec.

22. The system of claim 15, wherein the operations to perform correlating of a first signal segment in a first cardiac signal at a plurality of time offsets further comprise:
 generating a first reference segment from the first signal segment, the first reference segment extending from a beginning of the first signal segment to an ending represented by an end of the first signal segment minus a first time offset;
 determining a first correlation coefficient of the first signal segment that extends from the first time offset in the first signal segment to the end of the first signal segment against the first reference segment;
 generating a second reference segment from the first signal segment, the second reference segment extending from a beginning of the first signal segment to an ending represented by the end of the first signal segment minus a second time offset;
 determining a second correlation coefficient of the first signal segment that extends from the second time offset in the first signal segment to the end of the first signal segment against the second reference segment; and
 selecting the highest correlation coefficient for the first cardiac signal among the first correlation coefficient and the second correlation coefficient.

23. The system of claim 22, wherein the operations to perform correlating a first signal segment in a second cardiac signal at a plurality of time offsets further comprise:
 generating a first reference segment from the first signal segment, the first reference segment extending from a beginning of the first signal segment to an ending represented by an end of the first signal segment minus a first time offset;
 determining a first correlation coefficient of the first signal segment that extends from the first time offset in the first signal segment to the end of the first signal segment against the first reference segment;
 generating a second reference segment from the first signal segment, the second reference segment extending from a beginning of the first signal segment to an ending represented by the end of the first signal segment minus a second offset;
 determining a second correlation coefficient of the first signal segment that extends from the second time offset in the first signal segment to the end of the first signal segment against the second reference segment; and
 selecting the highest correlation coefficient for the second cardiac signal among the first correlation coefficient and the second correlation coefficient.

24. The system of claim 23, wherein the operations to perform generating a plurality of composite correlation coefficients comprise computing a sum of the highest correlation coefficient for the first cardiac signal and the highest correlation coefficient for the second cardiac signal.

25. The system of claim 23, wherein the operations to perform generating a plurality of composite correlation coefficients comprise computing a mean of the highest correlation coefficient for the first cardiac signal and the highest correlation coefficient for the second cardiac signal.

26. The system of claim 23, wherein the operations to perform generating a plurality of composite correlation coefficients comprise computing a square-mean-root of the highest correlation coefficient for the first cardiac signal and the highest correlation coefficient for the second cardiac signal.

27. The system of claim 15, wherein the plurality of composite correlation coefficients are generated using one of a sum, a mean and a square-mean-root of the highest correlation coefficients for the signal segments of the at least one first cardiac signal and the signal segments of the at least one second cardiac signal.

28. The system of claim 15, wherein the wherein the operations further comprise processing the set of signal segments to determine a source of a cardiac rhythm disorder.

* * * * *

UNITED STATES PATENT AND TRADEMARK OFFICE
CERTIFICATE OF CORRECTION

PATENT NO. : 10,368,764 B2
APPLICATION NO. : 14/483914
DATED : August 6, 2019
INVENTOR(S) : Carey Robert Briggs et al.

It is certified that error appears in the above-identified patent and that said Letters Patent is hereby corrected as shown below:

In the Claims

Claim 28, Column 27, Line 13:
Now reads: "wherein the wherein the operations"
Should read: -- wherein the operations --

Signed and Sealed this
Twenty-first Day of January, 2020

Andrei Iancu
*Director of the United States Patent and Trademark Office*